United States Patent
Kramer et al.

(10) Patent No.: US 10,905,827 B2
(45) Date of Patent: *Feb. 2, 2021

(54) INJECTION DEVICE WITH CAMMED RAM ASSEMBLY

(71) Applicant: Antares Pharma, Inc., Ewing, NJ (US)

(72) Inventors: Thomas Kramer, Andover, MN (US);
Matthew H. Rust, Hudson, WI (US);
Paul M. Goudreau, St. Paul, MN (US);
Peter A. Hoeft, Seattle, WA (US);
Julius C. Sund, Plymouth, MN (US);
Peter L. Sadowski, Woodbury, MN (US)

(73) Assignee: Antares Pharma, Inc., Ewing, NJ (US)

( * ) Notice: Subject to any disclaimer, the term of this patent is extended or adjusted under 35 U.S.C. 154(b) by 290 days.

This patent is subject to a terminal disclaimer.

(21) Appl. No.: 15/157,851

(22) Filed: May 18, 2016

(65) Prior Publication Data
US 2016/0263326 A1    Sep. 15, 2016

Related U.S. Application Data

(63) Continuation of application No. 13/889,183, filed on May 7, 2013, now Pat. No. 9,364,610.
(Continued)

(51) Int. Cl.
*A61M 5/20* (2006.01)
*A61M 5/30* (2006.01)
(Continued)

(52) U.S. Cl.
CPC ............ *A61M 5/2033* (2013.01); *A61M 5/20* (2013.01); *A61M 5/2053* (2013.01); *A61M 5/30* (2013.01);
(Continued)

(58) Field of Classification Search
CPC ...... A61M 5/24; A61M 5/2033; A61M 5/326; A61M 5/3146; A61M 5/31585;
(Continued)

(56) References Cited

U.S. PATENT DOCUMENTS 547,370 A    10/1895    Chalefou
1,465,793 A    8/1923    Schilling
(Continued)

FOREIGN PATENT DOCUMENTS

AR    00081651    10/2012
AR    082053      11/2012
(Continued)

OTHER PUBLICATIONS

International Patent Application No. PCT/US14/23883, International Search Report dated Jul. 10, 2014 (3 pages).
(Continued)

*Primary Examiner* — Bhisma Mehta
*Assistant Examiner* — Hong-Van N Trinh
(74) *Attorney, Agent, or Firm* — Morgan, Lewis & Bockius LLP

(57) ABSTRACT

An exemplary embodiment of injector includes a trigger mechanism, an energy source, and a user-operable firing-initiation member. The trigger member can include a trigger member having a retainer portion, and a ram assembly having a ram configured to pressurize a medicament container for expelling a medicament therefrom and a trigger engagement member configured to engage the retainer portion of the trigger member in a pre-firing condition. The energy source can be associated with the ram for powering the ram to expel the medicament, and the user-operable firing-initiation member can be operable for causing an axial rotation between the trigger engagement member and the retainer portion from the pre-firing condition to a firing
(Continued)

condition in which the trigger engagement member is released from the retainer portion to allow the energy source to fire the ram.

22 Claims, 28 Drawing Sheets

Related U.S. Application Data

(60) Provisional application No. 61/776,283, filed on Mar. 11, 2013, provisional application No. 61/763,395, filed on Feb. 11, 2013, provisional application No. 61/643,659, filed on May 7, 2012, provisional application No. 61/643,845, filed on May 7, 2012.

(51) Int. Cl.
*A61M 5/50* (2006.01)
*A61M 5/32* (2006.01)
*A61M 5/31* (2006.01)

(52) U.S. Cl.
CPC ........... *A61M 5/5086* (2013.01); *A61M 5/326* (2013.01); *A61M 2005/208* (2013.01); *A61M 2005/2013* (2013.01); *A61M 2005/2026* (2013.01); *A61M 2005/3125* (2013.01); *A61M 2202/0007* (2013.01); *A61M 2202/048* (2013.01)

(58) Field of Classification Search
CPC ........ A61M 2005/3247; A61M 5/3007; A61M 5/31581; A61M 5/31583; A61M 5/31586; A61M 5/20; A61M 2005/2013; A61M 2005/2026; A61M 2005/208; A61M 2005/202; A61M 2005/206; A61M 2005/2073; A61M 5/2053; A61M 5/30; A61M 5/5086; A61M 2005/3125; A61M 2202/0007; A61M 2202/048; A61M 2005/2407
See application file for complete search history.

(56) References Cited

U.S. PATENT DOCUMENTS

| | | |
|---|---|---|
| 1,512,294 A | 10/1924 | Marcy |
| 1,687,323 A | 10/1928 | Cook |
| 2,354,649 A | 8/1944 | Bruckner |
| 2,607,344 A | 8/1952 | Brown |
| 2,645,223 A | 7/1953 | Lawshe |
| 2,648,334 A | 8/1953 | Brown |
| 2,687,730 A | 8/1954 | Hein |
| 2,688,967 A | 9/1954 | Huber |
| 2,699,166 A | 1/1955 | Bickinson |
| 2,717,601 A | 9/1955 | Brown |
| 2,728,341 A | 12/1955 | Roehr |
| 2,737,946 A | 3/1956 | Hein, Jr. |
| 2,813,528 A | 11/1957 | Blackman |
| 2,866,458 A | 12/1958 | Mesa et al. |
| 2,888,924 A | 6/1959 | Dunmire |
| 2,893,390 A | 7/1959 | Lockhart |
| 3,130,724 A | 4/1964 | Higgins |
| 3,166,069 A | 1/1965 | Enstrom |
| 3,375,825 A | 4/1968 | Keller |
| 3,382,865 A | 5/1968 | Worrall |
| 3,526,225 A | 9/1970 | Hayamamachi |
| 3,557,784 A | 1/1971 | Shields |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | af Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |

(56) References Cited

U.S. PATENT DOCUMENTS

| | | | |
|---|---|---|---|
| 5,163,907 A | 11/1992 | Szuszkiewicz | |
| 5,176,643 A | 1/1993 | Kramer et al. | |
| 5,180,370 A | 1/1993 | Gillespie | |
| 5,185,985 A | 2/1993 | Vetter et al. | |
| 5,195,983 A | 3/1993 | Boese | |
| 5,221,348 A | 6/1993 | Masano | |
| 5,226,895 A | 7/1993 | Harris | |
| 5,232,459 A | 8/1993 | Hjertman | |
| 5,256,142 A | 10/1993 | Colavecchio | |
| 5,263,934 A | 11/1993 | Haak | |
| 5,271,744 A | 12/1993 | Kramer et al. | |
| 5,279,543 A | 1/1994 | Glikfeld et al. | |
| 5,279,576 A | 1/1994 | Loo et al. | |
| 5,279,585 A | 1/1994 | Balkwill | |
| 5,279,586 A | 1/1994 | Balkwill | |
| 5,281,198 A | 1/1994 | Haber et al. | |
| 5,290,228 A | 3/1994 | Uemura et al. | |
| 5,295,965 A | 3/1994 | Wilmot | |
| 5,300,030 A | 4/1994 | Crossman et al. | |
| 5,304,128 A | 4/1994 | Haber et al. | |
| 5,304,152 A | 4/1994 | Sams | |
| 5,308,341 A | 5/1994 | Chanoch | |
| 5,318,522 A | 6/1994 | D'Antonio | |
| 5,320,603 A | 6/1994 | Vetter et al. | |
| 5,330,431 A | 7/1994 | Herskowitz | |
| 5,332,399 A | 7/1994 | Grabenkort et al. | |
| 5,334,144 A | 8/1994 | Alchas et al. | |
| 5,342,308 A | 8/1994 | Boschetti | |
| 5,350,367 A | 9/1994 | Stiehl et al. | |
| 5,354,286 A | 10/1994 | Mesa et al. | |
| 5,358,489 A | 10/1994 | Wyrick | |
| RE34,845 E | 1/1995 | Vetter et al. | |
| 5,391,151 A | 2/1995 | Wilmot | |
| 5,405,362 A | 4/1995 | Kramer et al. | |
| 5,415,648 A | 5/1995 | Malay et al. | |
| 5,425,715 A | 6/1995 | Dalling et al. | |
| 5,451,210 A | 9/1995 | Kramer et al. | |
| 5,478,316 A | 12/1995 | Bitdinger et al. | |
| 5,505,694 A | 4/1996 | Hubbard et al. | |
| 5,514,097 A | 5/1996 | Knauer | |
| 5,514,107 A | 5/1996 | Haber et al. | |
| 5,540,664 A | 7/1996 | Wyrick | |
| 5,542,760 A | 8/1996 | Chanoch et al. | |
| 5,544,234 A | 8/1996 | Terajima et al. | |
| 5,549,561 A | 8/1996 | Hjertman | |
| 5,554,134 A | 9/1996 | Bonnichsen | |
| 5,562,625 A | 10/1996 | Stefancin, Jr. | |
| 5,567,160 A | 10/1996 | Massino | |
| 5,569,190 A | 10/1996 | D'Antonio | |
| 5,569,192 A | 10/1996 | van der Wal | |
| 5,569,236 A | 10/1996 | Kriesel | |
| 5,573,042 A | 11/1996 | De Haen | |
| 5,593,388 A | 1/1997 | Phillips | |
| 5,599,302 A | 2/1997 | Lilley et al. | |
| 5,599,309 A | 2/1997 | Marshall et al. | |
| 5,605,542 A | 2/1997 | Tanaka et al. | |
| 5,637,094 A | 6/1997 | Stewart, Jr. et al. | |
| 5,637,100 A | 6/1997 | Sudo | |
| 5,649,912 A | 7/1997 | Peterson | |
| 5,658,259 A | 8/1997 | Pearson et al. | |
| 5,665,071 A | 9/1997 | Wyrick | |
| 5,688,251 A | 11/1997 | Chanoch | |
| 5,695,472 A | 12/1997 | Wyrick | |
| 5,704,911 A | 1/1998 | Parsons | |
| 5,725,508 A | 3/1998 | Chanoch et al. | |
| 5,730,723 A | 3/1998 | Castellano et al. | |
| 5,743,889 A | 4/1998 | Sams | |
| 5,769,138 A | 6/1998 | Sadowski et al. | |
| 5,785,691 A | 7/1998 | Vetter et al. | |
| 5,788,670 A | 8/1998 | Reinhard et al. | |
| 5,801,057 A | 9/1998 | Smart et al. | |
| 5,807,309 A | 9/1998 | Lundquist et al. | |
| 5,820,602 A | 10/1998 | Kovelman et al. | |
| 5,820,622 A | 10/1998 | Gross et al. | |
| 5,827,232 A | 10/1998 | Chanoch et al. | |
| 5,836,911 A | 11/1998 | Marzynski et al. | |
| 5,843,036 A | 12/1998 | Olive et al. | |
| 5,846,233 A | 12/1998 | Lilley et al. | |
| 5,851,197 A | 12/1998 | Marano et al. | |
| 5,851,198 A | 12/1998 | Castellano et al. | |
| 5,860,456 A | 1/1999 | Bydlon et al. | |
| 5,865,795 A | 2/1999 | Schiff et al. | |
| 5,865,799 A | 2/1999 | Tanaka et al. | |
| 5,868,711 A | 2/1999 | Kramer et al. | |
| 5,873,857 A | 2/1999 | Kriesel | |
| 5,875,976 A | 3/1999 | Nelson et al. | |
| 5,879,327 A | 3/1999 | DeFarges et al. | |
| 5,891,085 A | 4/1999 | Lilley et al. | |
| 5,891,086 A | 4/1999 | Weston | |
| 5,893,842 A | 4/1999 | Imbert | |
| 5,919,159 A | 7/1999 | Lilley et al. | |
| 5,921,966 A | 7/1999 | Bendek et al. | |
| 5,925,017 A | 7/1999 | Kriesel et al. | |
| 5,928,205 A | 7/1999 | Marshall | |
| 5,935,949 A | 8/1999 | White | |
| 5,951,528 A | 9/1999 | Parkin | |
| 5,957,897 A | 9/1999 | Jeffrey | |
| 5,960,797 A | 10/1999 | Kramer et al. | |
| 5,989,227 A | 11/1999 | Vetter et al. | |
| 6,004,297 A | 12/1999 | Steenfeldt-Jensen et al. | |
| 6,045,534 A | 4/2000 | Jacobson et al. | |
| 6,056,716 A | 5/2000 | D'Antonio et al. | |
| 6,077,247 A | 6/2000 | Marshall et al. | |
| 6,083,201 A | 7/2000 | Skinkle | |
| 6,090,070 A | 7/2000 | Hager et al. | |
| 6,099,504 A | 8/2000 | Gross et al. | |
| 6,123,684 A | 9/2000 | Deboer et al. | |
| 6,132,395 A | 10/2000 | Landau et al. | |
| 6,159,181 A | 12/2000 | Crossman et al. | |
| 6,171,276 B1 | 1/2001 | Lippe et al. | |
| 6,203,529 B1 | 3/2001 | Gabriel et al. | |
| 6,210,369 B1 | 4/2001 | Wilmot et al. | |
| 6,221,046 B1 | 4/2001 | Burroughs et al. | |
| 6,221,053 B1 | 4/2001 | Walters et al. | |
| 6,223,408 B1 | 5/2001 | Vetter et al. | |
| 6,231,540 B1 | 5/2001 | Smedegaard | |
| 6,241,709 B1 | 6/2001 | Bechtold et al. | |
| 6,245,347 B1 | 6/2001 | Zhang et al. | |
| 6,258,078 B1 | 7/2001 | Thilly | |
| 6,264,629 B1 | 7/2001 | Landau | |
| 6,270,479 B1 | 8/2001 | Bergens et al. | |
| 6,309,371 B1 | 10/2001 | Deboer et al. | |
| 6,319,224 B1 | 11/2001 | Stout et al. | |
| 6,371,939 B2 | 4/2002 | Bergens et al. | |
| 6,383,168 B1 | 5/2002 | Landau et al. | |
| 6,391,003 B1 | 5/2002 | Lesch, Jr. | |
| 6,406,456 B1 | 6/2002 | Slate et al. | |
| 6,428,528 B2 | 8/2002 | Sadowski et al. | |
| 6,471,669 B2 | 10/2002 | Landau | |
| 6,494,865 B1 | 12/2002 | Alchas | |
| 6,517,517 B1 | 2/2003 | Farrugia et al. | |
| 6,530,904 B1 | 3/2003 | Edwards et al. | |
| 6,544,234 B1 | 4/2003 | Gabriel | |
| 6,562,006 B1 | 5/2003 | Hjertman et al. | |
| 6,565,553 B2 | 5/2003 | Sadowski et al. | |
| 6,568,259 B2 | 5/2003 | Saheki et al. | |
| 6,569,123 B2 | 5/2003 | Alchas et al. | |
| 6,569,143 B2 | 5/2003 | Alchas et al. | |
| 6,584,910 B1 | 7/2003 | Plass | |
| 6,589,210 B1 | 7/2003 | Rolfe | |
| 6,607,508 B2 | 8/2003 | Knauer | |
| 6,620,137 B2 | 9/2003 | Kirchhofer et al. | |
| 6,641,561 B1 | 11/2003 | Hill et al. | |
| 6,645,170 B2 | 11/2003 | Landau | |
| 6,656,150 B2 | 12/2003 | Hill et al. | |
| 6,673,035 B1 | 1/2004 | Rice et al. | |
| 6,682,504 B2 | 1/2004 | Nelson et al. | |
| 6,689,092 B2 | 2/2004 | Zierenberg et al. | |
| 6,706,000 B2 | 3/2004 | Perez et al. | |
| 6,746,429 B2 | 6/2004 | Sadowski et al. | |
| 6,767,336 B1 | 7/2004 | Kaplan | |
| 6,805,686 B1 | 10/2004 | Fathallah et al. | |
| 6,830,560 B1 | 12/2004 | Gross et al. | |
| 6,899,698 B2 | 5/2005 | Sams | |

(56) References Cited

U.S. PATENT DOCUMENTS

| | | |
|---|---|---|
| 6,932,793 B1 | 8/2005 | Marshall et al. |
| 6,932,794 B2 | 8/2005 | Giambattista et al. |
| 6,936,032 B1 | 8/2005 | Bush, Jr. et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,018,364 B2 | 3/2006 | Giambattista et al. |
| 7,066,907 B2 | 6/2006 | Crossman et al. |
| 7,112,187 B2 | 9/2006 | Karlsson |
| 7,118,552 B2 | 10/2006 | Shaw et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,220,247 B2 | 5/2007 | Shaw et al. |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,442,185 B2 | 10/2008 | Amark et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,500,964 B2 | 3/2009 | Shaw et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 8,496,619 B2 * | 7/2013 | Kramer ............... A61M 5/2033 604/135 |
| 9,364,610 B2 * | 6/2016 | KraMer ................ A61M 5/20 |
| 9,364,611 B2 * | 6/2016 | KraMer ................ A61M 5/20 |
| 9,446,195 B2 * | 9/2016 | Kramer ............... A61M 5/2033 |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Arnisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |

(56) References Cited

U.S. PATENT DOCUMENTS

| | | |
|---|---|---|
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0220524 A1 | 11/2004 | Sadwoski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0080377 A1 | 4/2005 | Sadowski et al. |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0106362 A1 | 5/2006 | Pass et al. |
| 2006/0129122 A1 | 6/2006 | Wyrick |
| 2006/0173408 A1* | 8/2006 | Wyrick ............... A61M 5/2033 604/110 |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0088288 A1 | 4/2007 | Barron et al. |
| 2007/0093775 A1 | 4/2007 | Daly |
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |
| 2008/0262427 A1 | 10/2008 | Hommann |
| 2008/0262436 A1* | 10/2008 | Olson ............... A61M 5/3202 604/198 |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch et al. |
| 2009/0304812 A1 | 12/2009 | Staniforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0056989 A1* | 3/2010 | McKay ............... A61B 17/3478 604/28 |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1* | 6/2010 | Julian ............... A61M 5/2033 604/506 |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Cleathero |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0157966 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |

(56) References Cited

U.S. PATENT DOCUMENTS

| | | |
|---|---|---|
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |
| 2014/0228769 A1* | 8/2014 | Karlsson ............ A61M 5/2033 604/197 |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |

(56) References Cited

FOREIGN PATENT DOCUMENTS

| | | |
|---|---|---|
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI0712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 10286399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1067823 | 1/2001 |
| EP | 1161961 | 12/2001 |
| EP | 1307012 | 5/2003 |
| EP | 1518575 | 3/2005 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| FR | 2506161 | 11/1982 |
| FR | 2635009 | 2/1990 |
| GB | 677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |

(56) References Cited

FOREIGN PATENT DOCUMENTS

| | | |
|---|---|---|
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012258628 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | 9714455 A1 | 4/1997 |
| WO | WO 97/14455 | 4/1997 |
| WO | WO 97/21457 | 6/1997 |
| WO | WO 1997/41907 | 11/1997 |
| WO | WO 97/48430 | 12/1997 |
| WO | WO 1998/031369 | 7/1998 |
| WO | WO 1998/032451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | WO 1999/062525 | 12/1999 |
| WO | WO 9962525 | 12/1999 |
| WO | WO 0006228 | 2/2000 |
| WO | WO 00/24441 | 5/2000 |
| WO | WO 00/29050 | 5/2000 |
| WO | WO 01/93926 | 12/2001 |
| WO | WO 02/083216 | 10/2002 |
| WO | WO 2002/089805 | 11/2002 |
| WO | WO 2089805 | 11/2002 |
| WO | WO 3047663 | 6/2003 |
| WO | WO 2003/070296 | 8/2003 |
| WO | WO 3068290 | 8/2003 |
| WO | WO 03070296 | 8/2003 |
| WO | WO 2003/097133 | 11/2003 |
| WO | WO 3097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |

(56) References Cited

FOREIGN PATENT DOCUMENTS

| | | |
|---|---|---|
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/086899 | 8/2006 |
| WO | WO 2006/125328 | 11/2006 |
| WO | WO 2006/130098 | 12/2006 |
| WO | WO 2007/047200 | 4/2007 |
| WO | 2007063342 A1 | 6/2007 |
| WO | WO 2007/063342 | 6/2007 |
| WO | WO 2007/100899 | 9/2007 |
| WO | 2007131013 A1 | 11/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |
| WO | WO 2008/107378 | 9/2008 |
| WO | WO 2008/112472 | 9/2008 |
| WO | WO 2007/104636 | 12/2008 |
| WO | WO 2009049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | 2010108116 A1 | 9/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | 2011060087 | 5/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | 2011095478 | 8/2011 |
| WO | 2011095480 | 8/2011 |
| WO | 2011095483 | 8/2011 |
| WO | 2011095486 | 8/2011 |
| WO | 2011095488 | 8/2011 |
| WO | 2011095489 | 8/2011 |
| WO | 2011095503 | 8/2011 |
| WO | 2011101349 | 8/2011 |
| WO | 2011101376 | 8/2011 |
| WO | 2011101377 | 8/2011 |
| WO | 2011101378 | 8/2011 |
| WO | 2011101379 | 8/2011 |
| WO | 2011101380 | 8/2011 |
| WO | 2011101381 | 8/2011 |
| WO | 2011101382 | 8/2011 |
| WO | 2011101383 | 8/2011 |
| WO | WO 2011/099918 | 8/2011 |
| WO | WO 2011/101351 | 8/2011 |
| WO | WO 2011/101375 | 8/2011 |
| WO | 2011107805 | 9/2011 |
| WO | 2011109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2011/051366 | 9/2012 |
| WO | WO 2012/122643 | 9/2012 |

OTHER PUBLICATIONS

International Patent Application No. PCT/US14/23485, International Search Report dated Jul. 7, 2014 (2 pages).
International Patent Application No. PCT/US14/24530, International Search Report dated Jul. 15, 2014 (2 pages).
International Patent Application No. PCT/US14/24543, International Search Report dated Jul. 28, 2014 (2 pages).
"Skin", American Medical Association (AMA) Current Procedural Terminology , 1998, http://www.ama-assn.org/ama/pub/category/print/7176.html, 1 page.
Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.

(56) References Cited

OTHER PUBLICATIONS

Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31 (6), pp. 361-366.
Hoekstra et al., Bioavailability of Higher Dose Methotrexate Comparing Oral and Subcutaneous Administration i n Patients with Rheumatoid Arthritis, The Journal of Rheumatology, 2004, 31(4), pp. 645-648.
International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.

"The Historical Development of Jet Injection and Envisioned Uses in Mass Immunization and Mass Therapy Based Upon Two Decades' Experience", Military Medicine, Jun. 1963, 128, pp. 516-524.
Pehling et al, "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US2013/029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Lunenfeld, "Stable Testosterone Levels Achieved with Subcutaneous Testosterone Injections", The aging Male, Mar. 2006, 9(1), 70 pages.
International Search Report dated Aug. 1, 2013 issued in connection with International Application No. PCT/US13/39976; International Filing Date: May 7, 2013.

* cited by examiner

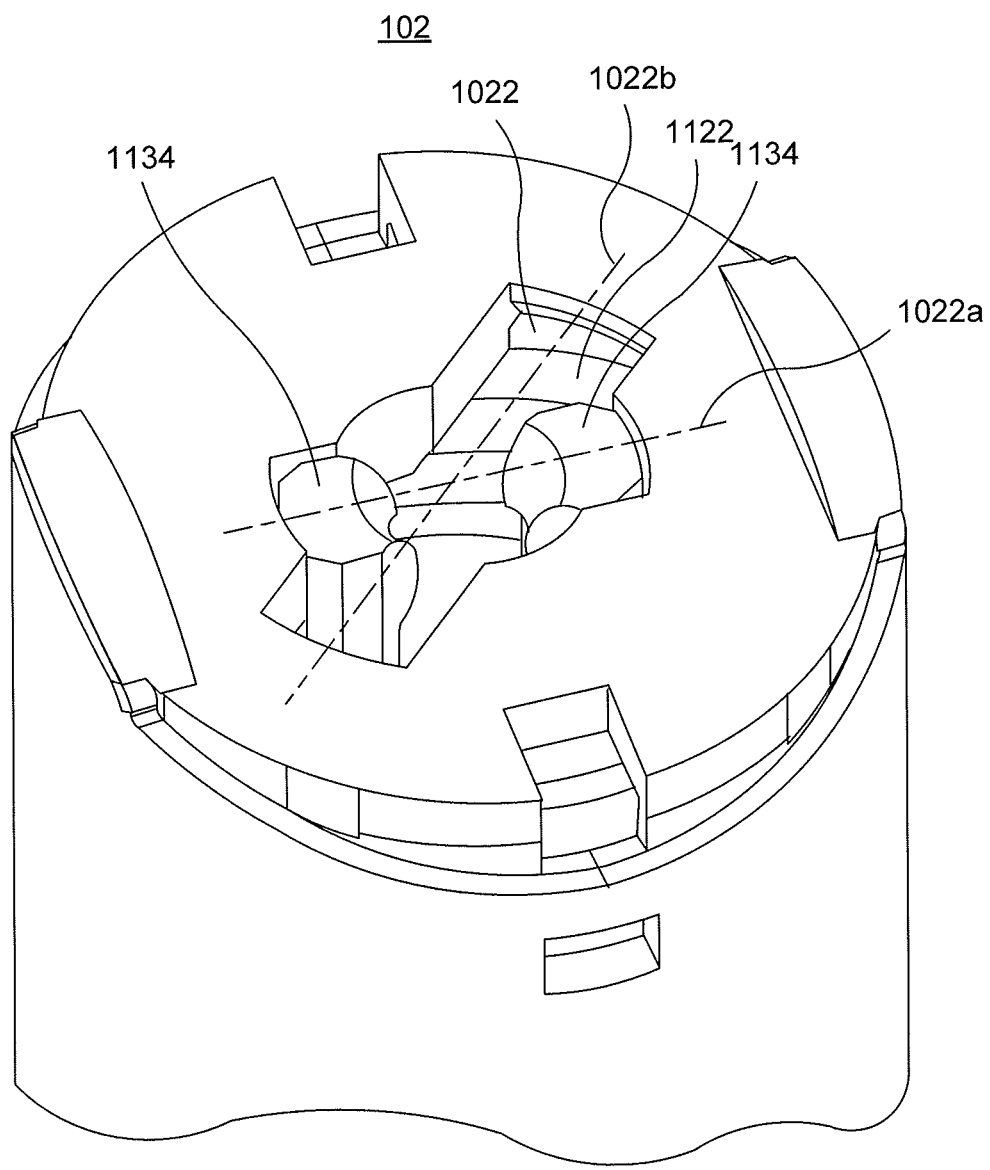
F I G. 2A

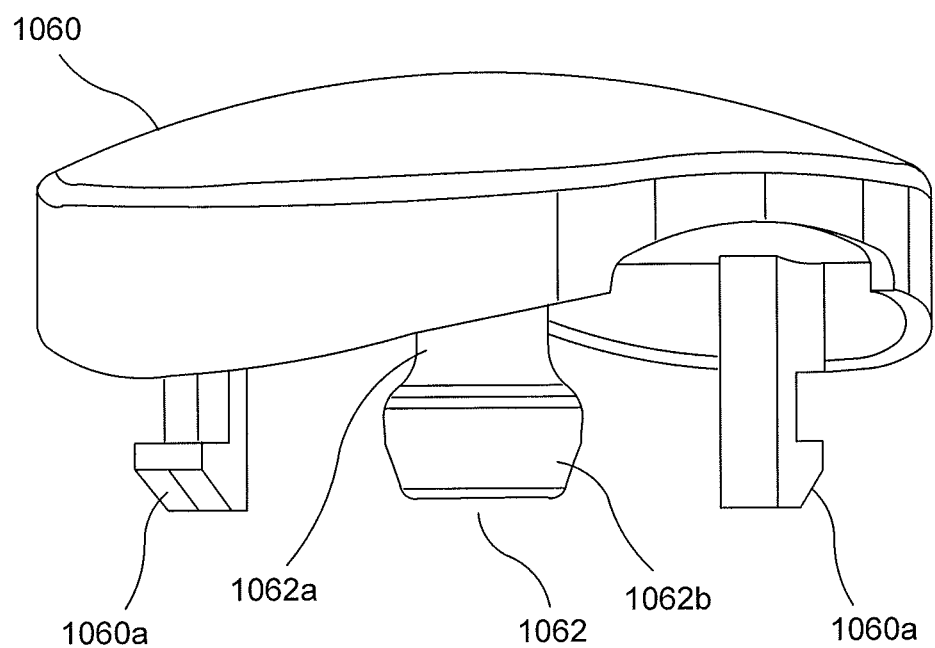
F I G. 3

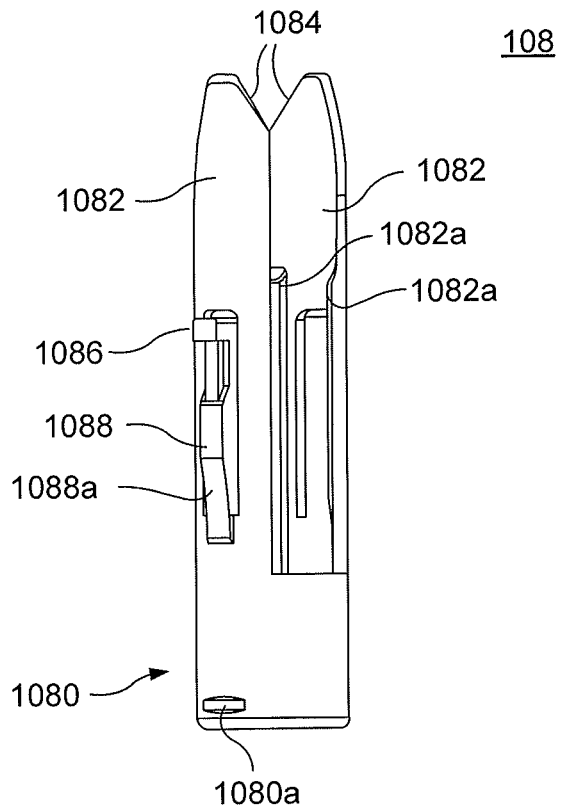
F I G. 5A
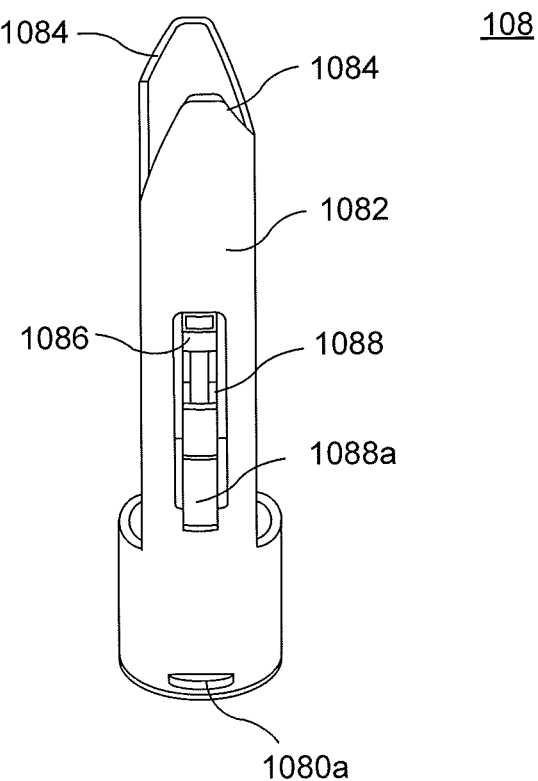
F I G. 5B

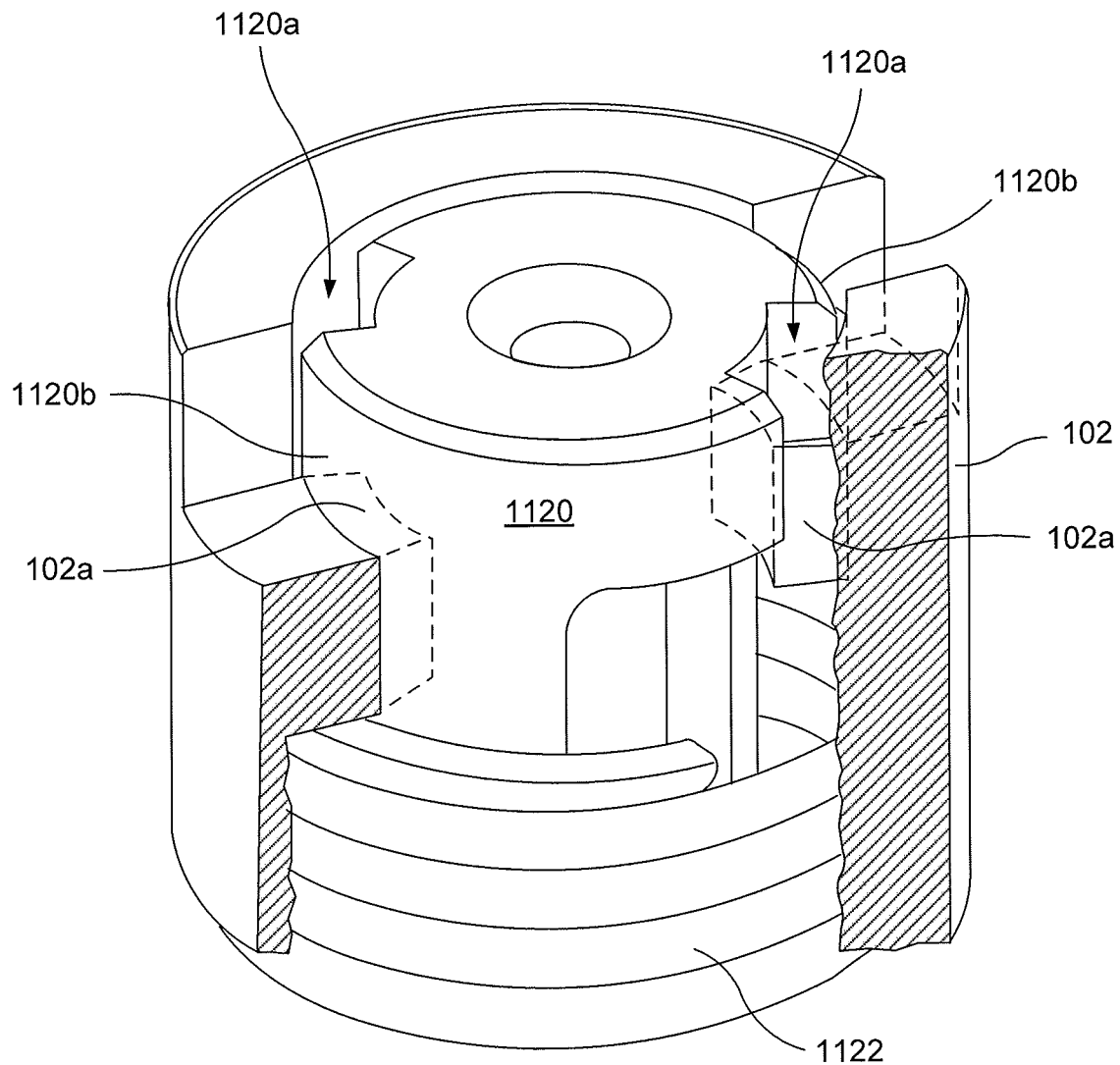
F I G. 18

INJECTION DEVICE WITH CAMMED RAM ASSEMBLY

CROSS-REFERENCE TO RELATED APPLICATIONS

This application is the continuation of U.S. patent application Ser. No. 13/889,183, filed 7 May 2013, which in turn claims benefit from U.S. Provisional Patent Application No. 61/643,659, filed 7 May 2012, U.S. Provisional Patent Application No. 61/643,845, filed 7 May 2012, U.S. Provisional Patent Application No. 61/776,283, filed 11 Mar. 2013, and U.S. Provisional Patent Application No. 61/763,395, filed 11 Feb. 2013, each of which is incorporated herein by reference in its entirety.

FIELD OF THE DISCLOSURE

The present disclosure relates to injection devices, and in particular to a needle assisted jet injector.

BACKGROUND INFORMATION

Various injection devices exist that employ an automated mechanism to actuate injection of a liquid medicament into a patient. Examples of such devices include jet injectors (both needle-free and needle-assisted) and traditional, low-pressure auto-injectors (that provide, for example, mechanized delivery of a traditional, finger-powered hypodermic syringe injection). Although the precise mechanisms used to complete an injection can vary, most include a feature that stores kinetic energy that can be used to drive an injection mechanism during use. Further, many injectors include a trigger mechanism configured to ensure that the kinetic energy remains stored until an injection is desired, whereby actuation of the trigger releases the injection mechanism, allowing the stored kinetic energy to drive the injection mechanism to cause injection.

Examples of needle-free jet injectors are described, for example, in U.S. Pat. Nos. 5,599,302; 5,062,830; and 4,790,824. These injectors administer medication as a fine, high velocity jet delivered under sufficient pressure to enable the jet to pass through the skin. The injection mechanism in such needle-free jet injectors can apply a force to a medicament storing chamber within the device such that the pressure required to inject the medicament is created within the chamber.

Traditional self-injectors or auto-injectors like the ones described, for example, in U.S. Pat. Nos. 4,553,962 and 4,378,015 and PCT Publications WO/9929720 and WO/9714455 inject medicament at a rate and in a manner similar to hand-operated hypodermic syringes. The described self-injectors or auto-injectors have needles that are extended at the time of activation to penetrate the user's skin to deliver medicament through movement of the drug container and related needle. Thus, the mechanism that provides the force to deliver the medicament in traditional, low-pressure self-injectors and auto-injectors can also be used to extend the needle and displace the drug container to cause the insertion of the needle through the user's skin and to apply a force to a plunger movably disposed within the drug container to cause the medicament to be expelled from the container through the needle. The auto-injectors manufactured, for example by Owen Mumford, thus use very low pressures to inject the medicament, which is typically injected through a needle in a relatively slow stream. Another self-injector includes the Simponi injector, which includes a window in the housing through which a yellow ram is visible inside a clear medicament container once the injector has been used.

Additionally, needle-assisted jet injectors have also been developed that utilize a needle to initially penetrate the skin, to the higher injection forces allowing but not restricted to an insertion depth less than that of a traditional hypodermic injector or low-pressure auto-injectors. Once the skin is penetrated with the needle, a jet mechanism is activated, causing the medicament containing liquid within the injector to be pressurized and expelled through the needle and into the skin. The injection mechanism in needle-assisted jet injectors can be configured to move the drug container and the needle forward to penetrate the skin and exert the necessary injection force to a plunger moveably disposed within the container. Alternatively, the needle and drug container can be positioned to penetrate the skin while keeping the needle and drug container in a stationary position, and the injection mechanism can be structured to pressurize the container. The pressure applied to the medicament within the injector can be less than that of a traditional jet injector, because the outer layers of the skin have already been penetrated by the needle. Similarly, the pressure applied to the medicament is preferably higher than that of a traditional auto-injector or the like, causing the medicament to penetrate the skin or the tissue below the skin to a depth that is sufficient so that the medicament remains substantially within the body. An additional benefit of the higher pressure includes a faster time of injection resulting in less psychological trauma to the patient and a decreased likelihood of the user inadvertently terminating the injection prematurely by removing the injector from the injection site.

Because of the stored energy associated with the trigger and injection mechanisms, accidental firing can occur due to sudden movements during shipping or due to mishandling of the device by a user including accidental actuation of the trigger mechanism. Accidental firing of the injection mechanism can cause the medicament to be expelled from the device, which can be at a dangerously high pressure, depending on the type of injection device. Further, accidental firing can cause an injection needle to move forward with respect to the device with sufficient force to penetrate the skin.

Additionally, the dimensions of many components incorporated in injectors typically constrain the design of many injectors. For example, many injectors utilize front triggering mechanisms that typically require an axial translation and engagement with a triggering structure located at the back of the injector. However, this configuration typically prevents binding of the communicating triggering components, which can be advantageous for, e.g., reducing the size of the injection device, being able to view the drug container within the device, etc.

SUMMARY

Exemplary embodiments of the present disclosure are directed to injection devices. An exemplary embodiment of the present disclosure can provide an injector including a trigger mechanism, an energy source, and a user-operable firing-initiation member. The trigger member can include a trigger member having a retainer portion, and a ram assembly having a ram configured to pressurize a medicament container for expelling a medicament therefrom and a trigger engagement member configured to engage the retainer portion of the trigger member in a pre-firing condition. The energy source can be associated with the ram for powering the ram to expel the medicament, and the user-operable firing-initiation member can be operable for causing an axial rotation between the trigger engagement member and the retainer portion from the pre-firing condition to a firing condition in which the trigger engagement member is released from the retainer portion to allow the energy source to fire the ram. The exemplary injector can further include an injection housing, where the trigger engagement member and the ram are in fixed association, such that rotation of the trigger engagement member rotates the ram, and the ram assembly is associated with the firing-initiation member such that operation of the firing-initiation member rotates the ram assembly within the housing to the firing condition.

The exemplary injector can further include an injector housing. The firing initiation member can also include a skin-contacting member disposed at a distal end of the injector that is movable proximally with respect to the housing when a force is applied to the skin-contacting member at the distal end of the injector. Further, the firing initiation member can be associated with the trigger mechanism and configured to cause the axial rotation between the trigger engagement member and the retainer portion from the pre-firing condition to the firing condition upon a proximal movement of the skin-contacting member with respect to housing. Additionally, the skin-contacting member can include a needle guard that is retractable and is configured to expose a needle connected to the medicament container upon the proximal movement of the skin-contacting member.

According to another exemplary embodiment of the present disclosure, the needle can be in fluid communication with the medicament container for injecting the medicament expelled therefrom during the firing. Further, the energy source and the needle can be configured for jet injecting the medicament through the needle. The energy source can be configured to pressurize the medicament to between about 90 p.s.i. and about 500 p.s.i. to jet inject the medicament, and the energy source and needle can be configured for injecting the medicament at an average velocity of at least about 1,000 cm/sec within the needle.

According to another exemplary embodiment of the present disclosure, the skin contacting member can include a first cam, and the ram assembly can include a second cam. The first cam can be operatively associated with the second cam for camming the second cam upon the axial movement to rotate the ram assembly with respect to the retainer portion so as to position the ram assembly in the firing condition. The trigger mechanism can include a ram holding member that axially retains the ram assembly in a proximal position against action of the energy source in the pre-firing position, the retainer portion retaining the trigger engagement member engaged and held against firing by the ram holding member. Additionally, in the firing condition, the ram can be disengaged from the retainer portion, and the energy source overcomes an engagement between the trigger engagement member and the ram holding member. Further, the ram holding member can include a projection that includes a bulge and a groove engaged with the trigger engagement member, and the retainer portion retaining said engagement of the trigger engagement member with the bulge and groove, in the pre-firing condition.

According to certain exemplary embodiments of the present disclosure, the ram assembly can be of unitary construction.

According to yet another exemplary embodiment of the present disclosure, the injector can further include a container support that is configured for holding the medicament container during injection, and wherein the ram assembly is configured to engage the container support to lock-out the injector after an injection. Further, proximal movement of the user-operable firing-initiation member can be blocked by the ram assembly when the injector is locked-out.

According to yet another exemplary embodiment of the present disclosure, a pre-firing color gamut is visible from the exterior of the injector in the pre-firing condition. Further, the injector can further include a housing including a window; and an indicator having an indicator color that is absent from the pre-firing color gamut, which color is hidden from view within the housing in the pre-fired condition, and in the fired condition, the indicator color is visible through the window from the exterior of the injector for indicating the fired condition. In certain embodiments, the ram assembly can include the indicator, and the ram assembly can entirely occlude the window in the fired condition.

Yet another exemplary embodiment of the present disclosure can provide an injector including a trigger mechanism having a trigger member having a retainer portion, and a ram assembly having a ram configured to pressurize a medicament container for expelling a medicament therefrom and at least one first camming surface. The ram assembly can further include a trigger engagement member configured to engage the retainer portion of the trigger member in a pre-firing condition. The injector can further include an energy source associated with the ram for powering the ram to expel the medicament, and a needle guard including a user-operable firing-initiation member operable having at least one second camming surface configured to operatively associate with the at least one first camming surface so as to cause an axial rotation between the trigger engagement member and the retainer portion from the pre-firing condition to a firing condition in which the trigger engagement member is released from the retainer portion to allow the energy source to fire the ram. The injector can further include a container support, and the ram assembly can be configured to engage the container support to lock-out the injector after an injection.

BRIEF DESCRIPTION OF THE DRAWINGS

These and other objects, features and advantages of the invention will be apparent from a consideration of the following non-limiting detailed description considered in conjunction with the drawing figures, in which:

FIG. 2A is a perspective view of a proximal portion of an exemplary injection device according to an exemplary embodiment of the present disclosure;

FIG. 3 is a side view of an end housing portion of an exemplary injection device according to an exemplary embodiment of the present disclosure;

FIGS. 5A and 5B are side and perspective views respectively of a needle guard of an exemplary injection device according to an exemplary embodiment of the present disclosure;

FIG. 18 shows a partially cut-away perspective view of a proximal portion of an exemplary injection device according to another embodiment of the present disclosure.

Figure 1A:
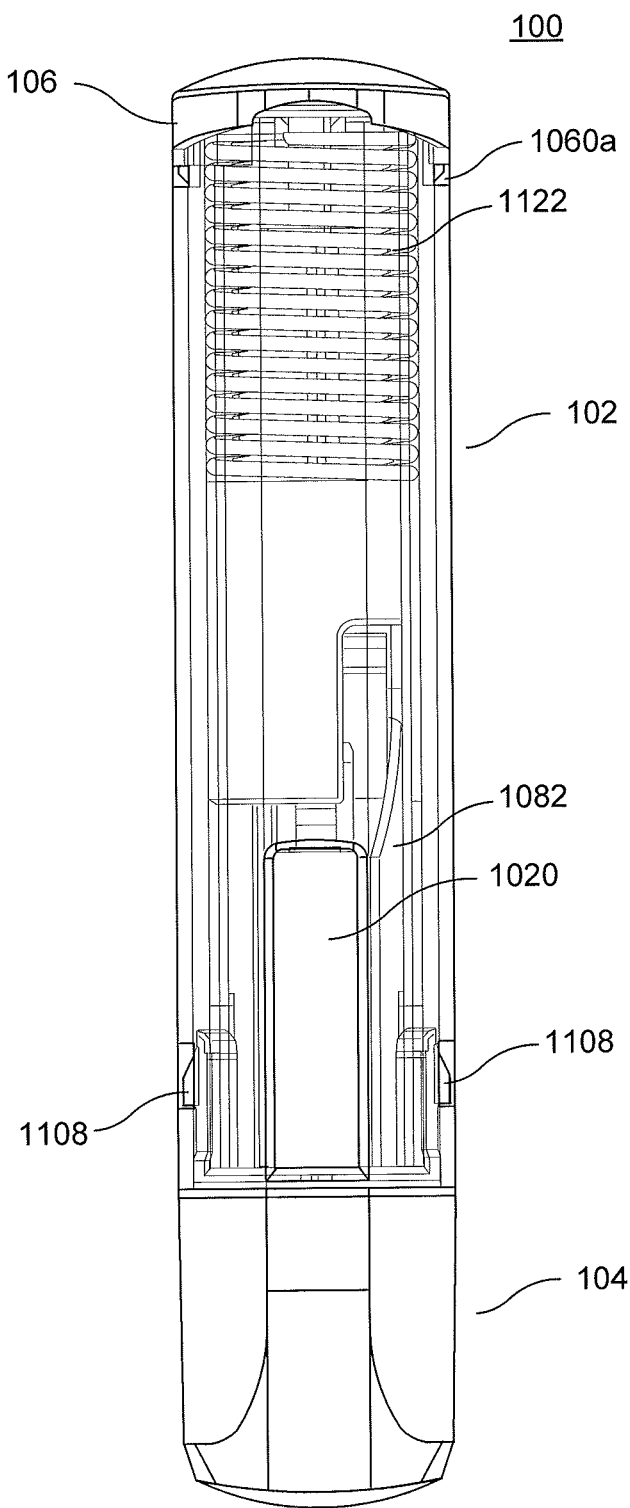
FIG. 1A is a side partial cross-sectional view of an exemplary injection device according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

FIG. 1A shows an exemplary injection device 100 according to an exemplary embodiment of the present disclosure. It is noted that, in the context of this disclosure, the terms "distal" and "proximal" are used in reference to the position of the injection device relative to a user of the injection device when merely held by a user. Accordingly, a point located distal to a second point would be further from the user (i.e., towards an injection end of the injection device) and vice versa. As shown in the drawings, the exemplary injection device 100 is preferably a needle assisted jet injection device, although a person having ordinary skill in the art will understand alternative embodiments employing certain features herein can be configured as needle-free jet injectors, or as low-pressure auto-injectors or other mechanized injectors. According to certain exemplary embodiments, injection device 100 can be a one-time disposable needle-assisted jet injector with a lock-out feature. For example, injection device 100 can facilitate a jet injection of medicament stored within injection device 100 and can include a locking feature that prevents a user from attempting to use injection device 100 once the medicament has been dispensed. Preferably, the locking feature is activated upon dispensing of the medicament and not upon use of injection device 100. For example, the locking feature can be activated, thus preventing injection device 100 from a subsequent attempted use by a user, even in the case where the injection device was not used by a user for an injection, but where a firing mechanism was inadvertently activated (e.g., during transport, handling, etc. of the device) and the medicament was dispensed. Operation of injection device 100, including the locking feature, is described in further detail below.

According to certain exemplary embodiments, injection device 100 can deliver any suitable liquid drug or medicament. Further, injection device 100 can allow the injection to be administered by individuals that do not have formal training (e.g., self-administered or administered by another individual family member or other caregiver who may not be a formally trained healthcare provider, such as a parent administering a drug to a child). Accordingly, injection device 100 can be useful in situations where self-injections/caregiver administered injections would be beneficial, including, but not limited to, low T, hypogonadism, diabetes, infertility treatment, sexual dysfunction, cardiovascular disease, oncology supportive care, allergic reaction, multiple sclerosis, rheumatoid arthritis psoriasis, other autoimmune conditions including Crohn's disease and SLE, chronic pain, migraine, epileptic seizure, kidney disease, and the like. Further, injection device 100 can be used to inject a wide range of drugs. For example, injection device 100 can be used to inject drugs, water soluble medicaments and oil soluble medicaments. In one embodiment, the medicament includes a benzodiazepine, including midazolam. In another embodiment, the medicament is dissolved in oil instead of aqueous solutions, and can include hormone drugs used in men (e.g., testosterone, or a derivative or ester thereof) and women; small molecule injectable drugs such as, methotrexate (see, e.g., International Publication No. WO 2010/108116, which is incorporated by reference herein in its entirety); and/or biological drugs, including those having a high viscosity. Further, and as noted above, injection device 100 can be used to inject androgens, including testosterone formulations (e.g., testosterone cypionate and testosterone enanthate).

Testosterone is a steroid hormone from the androgen group. In general, androgens promote protein synthesis and growth of those tissues with androgen receptors. Testosterone is anabolic, meaning it builds up bone and muscle mass. Testosterone has the following structural formula:

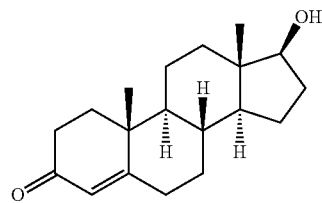

The original and primary use of testosterone is for the treatment of males who have too little or no natural endogenous testosterone production—males with Low T or hypogonadism. According to the Massachusetts Male Aging Study, about 6% to 12% men aged 40 to 60 years have symptomatic low testosterone deficiency. However, over the years, testosterone has also been given for many other conditions, e.g., reducing infertility, correcting lack of libido or erectile dysfunction, correcting osteoporosis, encouraging penile enlargement, encouraging height growth, encouraging bone marrow stimulation, reversing the effects of anemia and appetite stimulation.

In certain embodiments, injection device 100 can be used to inject one or more of epinephrine, atropine, dihydroergotamine, sumatriptan, antibiotics, antidepressants, anticoagulants, glucagon, diazepam, haloperidol, apomorphine, lovenox, and toradol. In other embodiments, injection device 100 can be used to inject biosimilar, biological and or peptide drugs, including without limitation Enbrel, Humira, Lantus, Epogen (Procrit), Neulasta, Aranesp, Avonex, PEGasys, Rebif, Neupogen, Betaseron, Avastin, Remicade, Herceptin, Erbitux, Recombinate, Cerezyme, NovoSeven, Tysabri, Synagis, Copaxone and Kogenate FS.

In other embodiments, injection device 100 can be used to inject parathyroid hormone ("PTH") and various other medications such as exenatide and the like. Injection device 100 can also be used to inject medicaments listed in the Physicians' Desk Reference (PDR®), 67th Edition (2013) (which is herein incorporated by reference in its entirety), and, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antiviral antibiotics, anticancer preparations, anticholinergic drug inhibitors, anticoagulants, anticonvulsants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antineoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, biosimilars, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, diazepam, epinephrine expectorants and combinations, diuretics, emetics, enzymes and digestants, fertility agents, fluorine preparations, galactokinetic agents, general anesthetic, geriatrics, germicides, hematinics, hemorrhoidal preparations, histamine H receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®. Some other medicaments that can be used with injector device 100 include Ergocalciferol (Calciferol), diethylstilbestrol, Diprovan (propofol), estradiol valerate, fluphenazine decanoate, fulvestrant, intralipid, liposyn, nandrolone decanoate, nebido, nutralipid, paclitaxel, progesterone, prograf, testosterone cypionate, zuclopenthixol, and haloperidol dodecanoate. In certain embodiments, the medicament is dissolved in soybean oil, ethyl oleate, castor oil, sesame oil, safflower oil, arachis oil, polyoxyethylated castor oil (Cremophor® EL), polyoxyl 60 hydrogenated castor oil (HCO-60), cottonseed oil, or thin oil derived from coconut oil.

In some embodiments, the medicament may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with injection device 100 in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, duboisia hopwoodii, prosanthera striatiflora, kava (*piper methysticum*), mandrake, valerian, and marijuana, non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexaenoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia hopwoodii, prosanthera striatiflora, kava (*piper methysticum*), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

While injection device 100 can deliver an injection of up to approximately 1 mL per injection, other volumes can be injected in alternative embodiments.

According to certain exemplary embodiments, injection device 100 can be configured to inject medicament stored within a prefilled syringe. Prefilled syringes that are manufactured by a blown glass process can have significant dimensional tolerances and unevenness. Accordingly, features of injection device 100 can serve to accommodate the shape irregularities and to properly position and locate a prefilled syringe within injection device 100. Further, injection device 100 can be configured as a needle-assisted jet injector, providing a peak pressure during the injection of less than about 1,000 p.s.i., preferably less than 500 p.s.i., and more preferably less than about 350 p.s.i. At an end of an injection, the pressure applied to the medicament is preferably at least about 80 p.s.i., more preferably at least about 90 p.s.i., and most preferably at least about 100 p.s.i. In one embodiment, the initial pressure can be around 330 p.s.i., and the final pressure can be about 180 p.s.i., while in another embodiment the initial pressure can be about 300 p.s.i., dropping to around 110 p.s.i. at the end of the injection. These exemplary pressures can, for example, result in a flow rate of about 0.2 mL/sec to 0.75 mL/sec, and preferably about 0.5 mL/sec. The needles used are preferably between 26 and 28 gauge, and are most preferably around 27 gauge, but alternatively other needle gauges can be used where the other components are cooperatively configured to produce the desired injection. In preferred jet injector embodiments firing aqueous medicaments, the firing mechanism, medicament container, needle, and energy source are configured to produce an average stream velocity within the needle of at least about 1,000 cm/sec, and more preferably at least about 1,500 cm/sec, up to about 5,000 cm/sec, and more preferable up to about 3,000 cm/sec. In one embodiment, the average stream velocity during injection is about or reaches between about 1,800 and 2,200 cm/sec or approximately 2,000 cm/sec. The velocities used to produce a jet injection will vary for other types of medicaments, such as based on their viscosities. Weaker energy sources, and/or larger needles, for example, can be used to obtain lower velocities and lower pressures and/or flow rates for traditional, low-pressure autoinjector embodiments. Such embodiments can also benefit from the axial rotation between the trigger engagement member and the retainer portion, while moving from the pre-firing condition to the firing condition upon a proximal movement of the skin-contacting member with respect to housing.

Figure 1B:
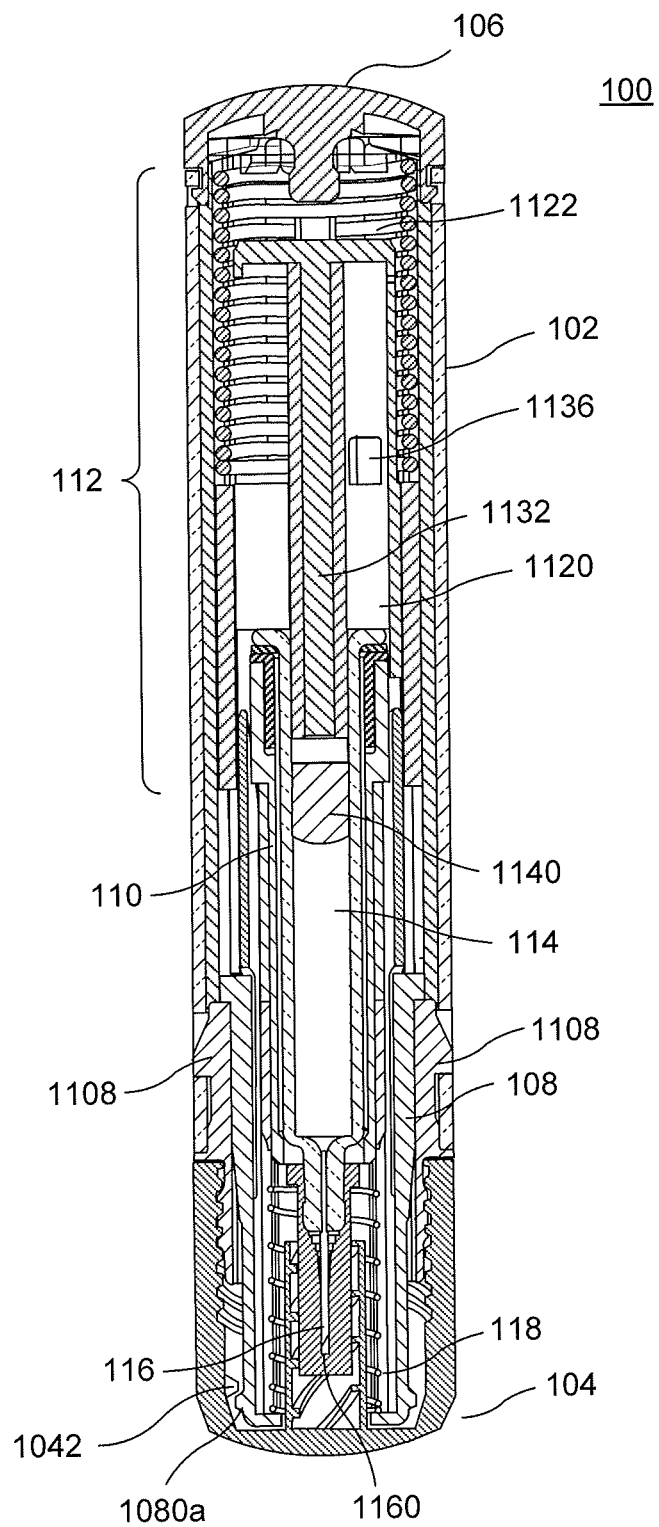
FIG. 1B is a cross-sectional view of an exemplary injection device according to an exemplary embodiment of the present disclosure.

As shown in FIG. 1B, the exemplary injection device 100 can include an outer housing 102, a cap 104, and a housing end/end cap 106. Injection device 100 can further include various components and/or assemblies housed within outer housing 102. As shown in FIG. 1B, these components can include a guard 108, a container support, such as, e.g., a sleeve 110, a firing mechanism 112, a medicament chamber 114, a needle 116, and a spring 118. As shown in FIG. 1A, outer housing 102 can be a single piece component, or alternatively, outer housing 102 multiple piece assembly that can be coupled together, for example, via a snap-fit connection, a press-fit connection, a threaded engagement, adhesives, welding, or the like.

Figure 14:
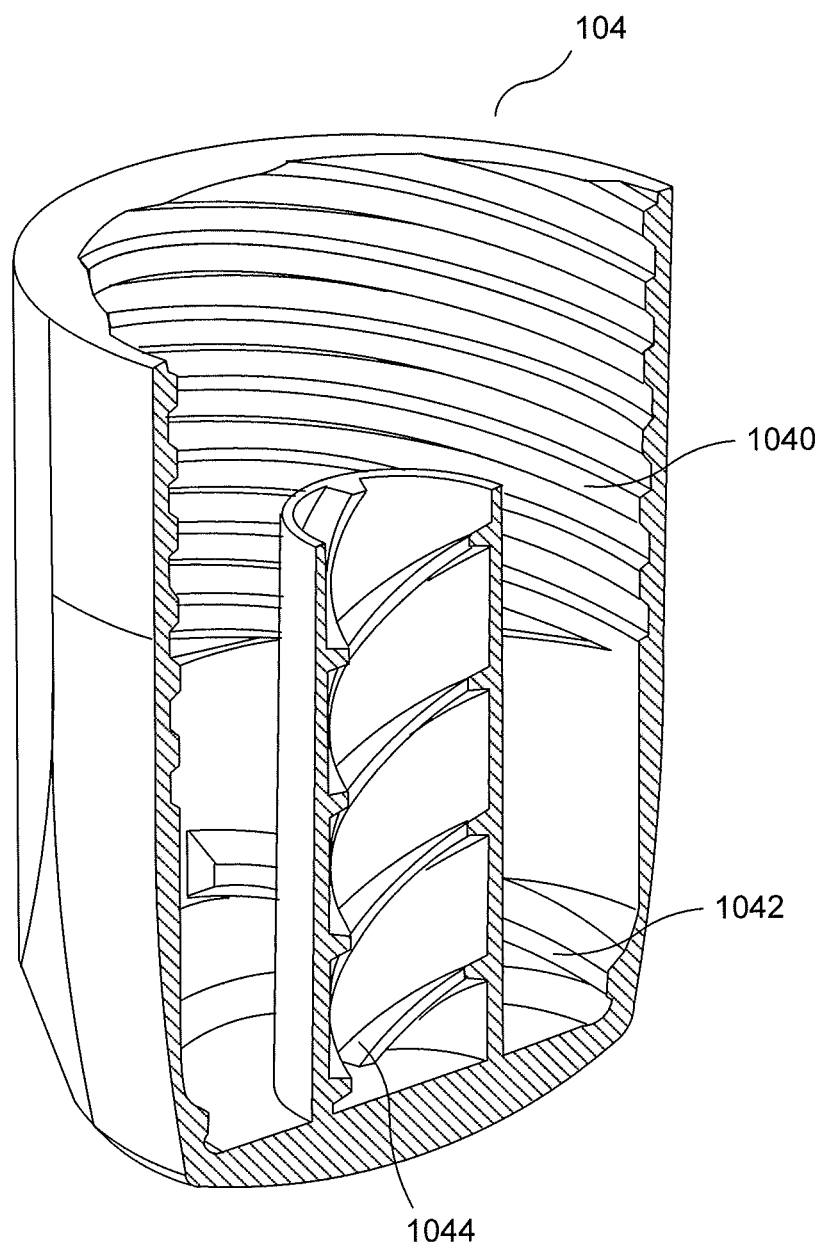
FIG. 14 shows a cross sectional view of a cap of an exemplary injection device according to an exemplary embodiment of the present disclosure.

As shown in FIG. 1B, cap 104 is removably affixable to a distal end of outer housing 102, and housing end/end cap 106 is coupled to a proximal end of housing 102. For example, cap 104 can be removably affixed to the distal end of housing 102 via a threaded engagement and housing end 106 can include features (e.g., projections) configured to engage a portion of the proximal end of housing 102 (e.g., openings) to couple housing end/end cap 106 to housing 102. When affixed to injection device 100, cap 104 can ensure that an injection is not triggered by an inadvertent application of a force to guard 108. Preferably, cap 104 includes two engagement features. As shown in FIG. 14, cap 104 can include engagement features 1040 and 1042. Engagement features 1040 and 1042 can be threads configured to threadedly engage other features of injection device 100. For example, engagement feature 1040 can be configured secure cap 104 to the distal end of housing 102 (e.g., via a threaded engagement with a distal portion of sleeve 110), and engagement feature 1042 can be configured to threadedly engage features of guard 108 to prevent proximal displacement of guard 108. For example, FIG. 1B shows feature 1042 engaged with feature 1080a of guard 108, thereby preventing proximal movement of guard 108, such as may occur if the injector is accidentally dropped or otherwise jolted.

Additionally, cap 104 is preferably non-circular in cross-section viewed along its axis and in the initial, closed position aligns with or substantially matches the shape of the portion of the housing adjacent thereto. Features 1040 can include a plurality of threads, having more than one thread starting point, only one of which will result in the cap lining up with the housing as in the initial closed position. Consequently, if the cap is removed and replaced, there is a chance that an incorrect starting point will be selected by the user, resulting in the cap no longer aligning with the injector housing, and providing an indication of tampering. In one embodiment, three threads are used, so there is a two in three chance that a removed and replaced cap will become immediately obvious based on an ill-fitting cap.

Figure 1C:
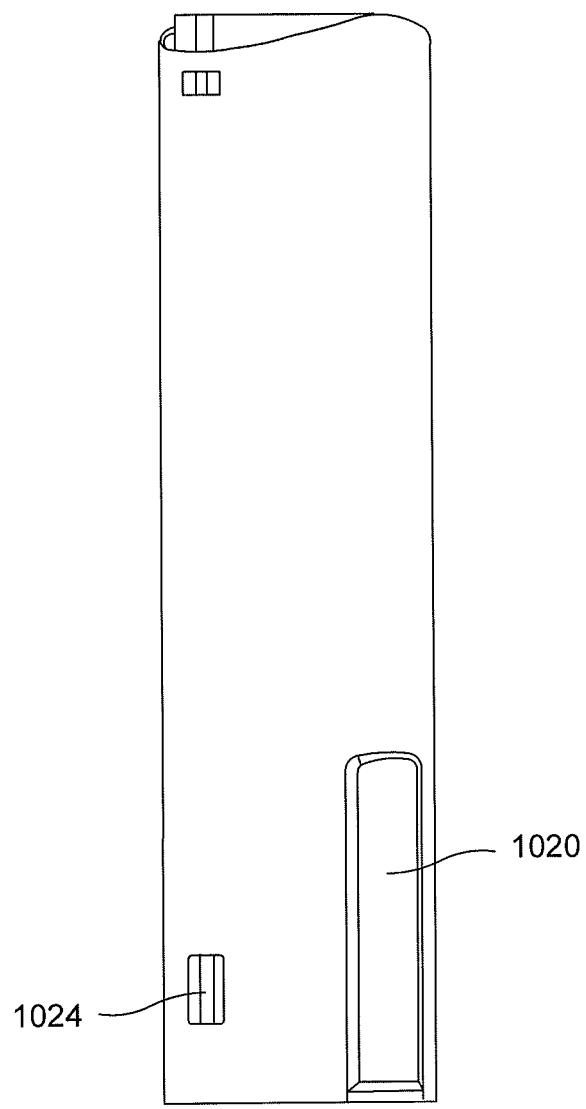
FIG. 1C is a side view of a housing of an exemplary injection device according to an exemplary embodiment of the present disclosure.

As shown in FIG. 1C, housing 102 can include openings 1024 configured to engage with sleeve 110 to couple and secure sleeve 110 to housing 102 and can include at least one window 1020 that can provide a visual indication of whether or not injection device 100 has been fired. For example, in an unfired state, window 1020 can allow a user to see medicament chamber 114, along with the stored medicament, and in a fired state, window 1020 can show one or more internal components, such as a portion of firing mechanism 112, which can be a color specifically selected to alert the user that injection device 100 has been fired, and is preferably sufficiently different than other colors visible to a user (preferably having ordinary eyesight) on the injector prior to firing, so as to be conspicuously different to, or contrast from, any other colors present or significantly present. For example, the color can differ from all the other components of injection device 100 pre-firing, or visible by the user pre-firing, so as to be conspicuous (e.g., introducing an entirely new color family). The new color appearing after firing, can be from a non-analogous part of the color wheel, or can contrast, or can be a complementary color, with respect to the colors visible on injection device 100. The new color can signify caution, such as red or orange, etc. In one embodiment, the colors visible on the injector in the pre-firing condition, preferably including when the cap 104 is on and/or off the injector, are grays and blues, for instance. When the injector is fired, the color red can be introduced. Preferably, this new color can be introduced after firing but prior to guard 108 being locked-out in the extended position.

Figure 2B:
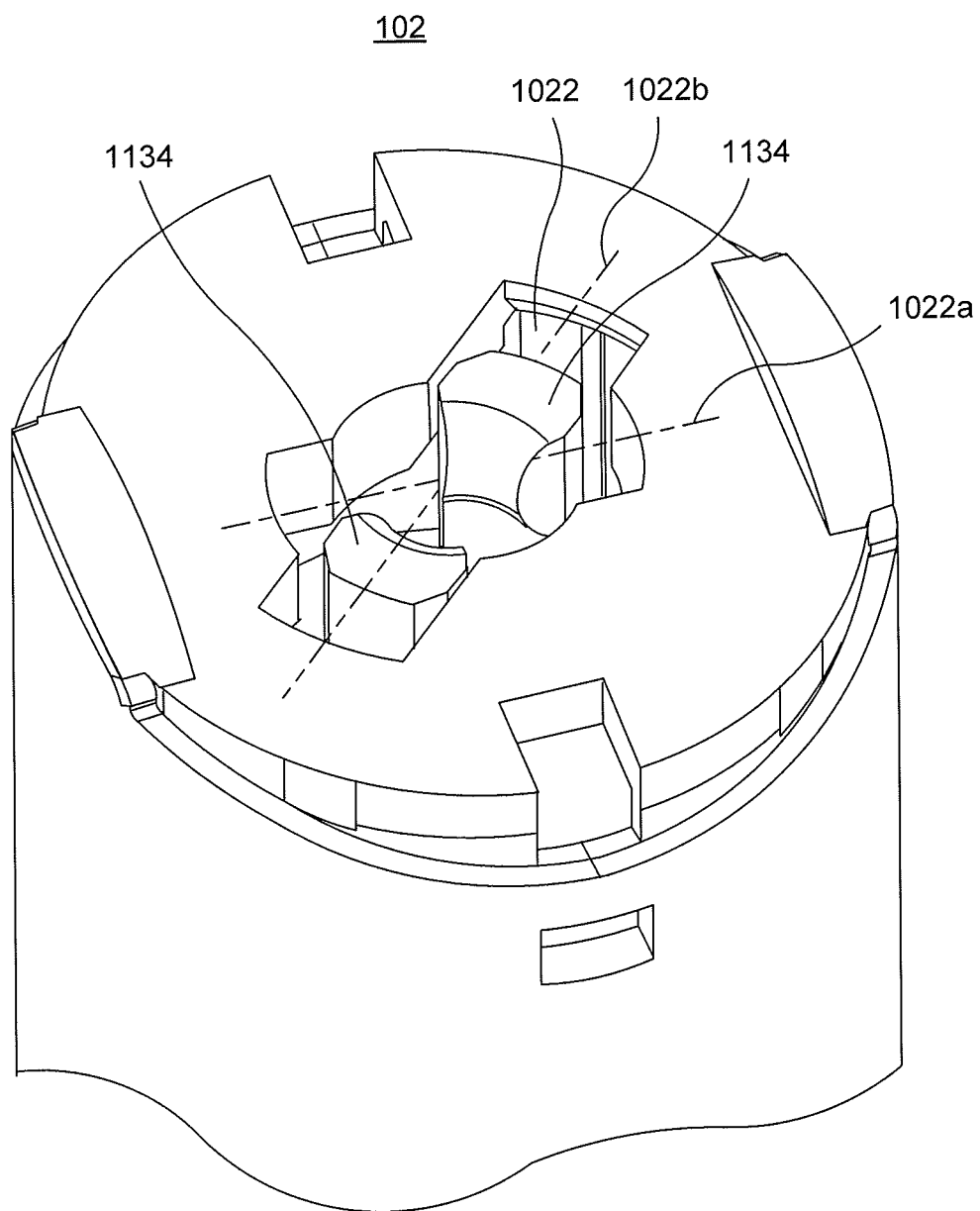
FIG. 2B is another perspective view of a proximal portion of an exemplary injection device according to an exemplary embodiment of the present disclosure.

A proximal end of housing 102 can also include a trigger member, which can include a trigger member retaining portion 1022. For example, trigger member retaining portion 1022 can include an opening configured to receive and engage at least a trigger engagement member of firing mechanism 112 (e.g., projections) in facilitating firing of injection device 100. Opening 1022 is preferably configured to engage a trigger engagement member, e.g., projections 1134 of firing mechanism 112, for example latch tabs, such that they are aligned in one of two positions. For example, in first position 1022a (e.g., retaining position), the opening can include retaining portions so that projections 1134 of firing mechanism 112 are aligned so that they can be restrained by lateral sides of opening 1022, thereby preventing firing mechanism 112 from firing (e.g., by preventing projections 1134 from splaying open firing mechanism 112 is prevented from slidably displacing under a force exerted by an energy source) and dispensing the medicament. In second position 1022b (e.g., firing position), the opening can include firing portions such that the projections of firing mechanism 112 are aligned such that projections can splay apart, thereby permitting firing mechanism 112 to fire. FIG. 2A shows projections 1134 aligned in the first position (1022a) and FIG. 2B shows projections 1134 aligned in the second position (1022b). Further, the lateral walls of the retaining portions of the opening (e.g., in the first position 1022a) are preferably curved to facilitate rotation of projections 1134 between the first and second positions.

Injection device 100 also preferably includes housing end/end cap 106. As shown in FIG. 3, housing end/end cap 106 preferably includes a body portion 1060 and a ram holding member 1062. Ram holding member 1062 can be a projection, and can be configured to engage a trigger engagement member of firing mechanism 112. For example, ram holding member 1062 can be a bell-shaped projection, and can engage a complementary shaped feature (e.g., projections) of firing mechanism 112. In an exemplary embodiment, ram holding member 1062 can include a groove 1062a and a bulge 1062b, and features of firing mechanism 112 can be configured to align with groove 1062a so as to hold bulge 1062b to prevent firing of injection device 100. Preferably, ram holding member 1062 and the features of firing mechanism 112 engaging with ram holding member 1062 include a circular cross section to allow rotation of the features of firing mechanism 112 relative to ram holding member 1062 during firing of injection device 100. Further, body portion 1060 can include projections 1060a configured to engage openings in outer housing 102 to couple housing end/end cap 106 to housing 102. In an exemplary embodiment.

Figure 4A:
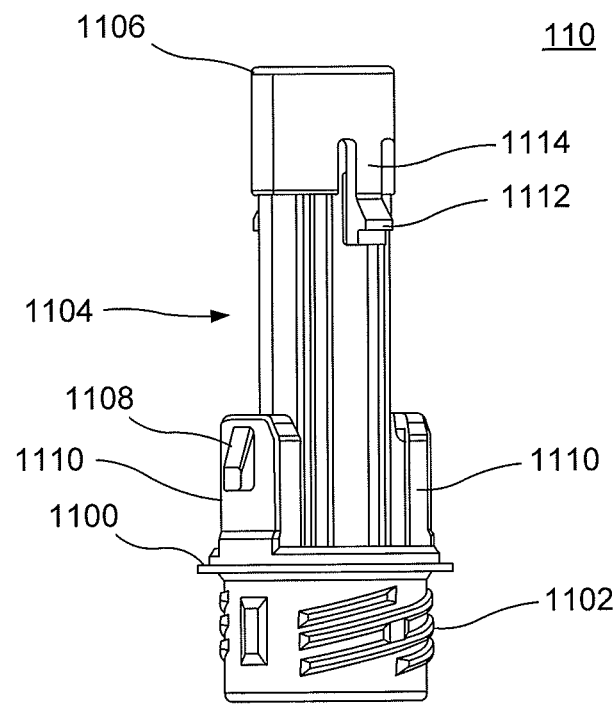
FIGS. 4A and 4B are side and perspective views respectively of a front housing portion and a sleeve of an exemplary injection device according to an exemplary embodiment of the present disclosure.
Figure 4B:
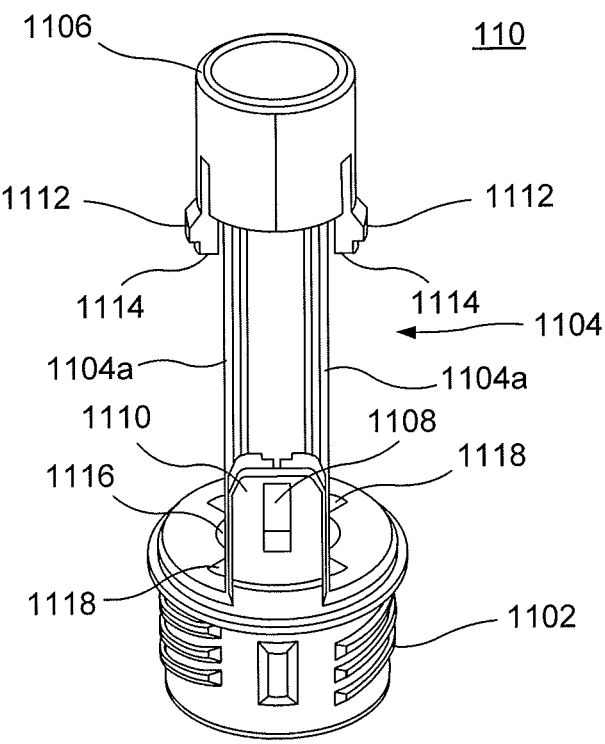

As shown in FIG. 1B, sleeve 110 is preferably at least partially housed within outer housing 102 and mounted to outer housing 102 via, for example, a snap-fit connection, a press-fit connection, a threaded engagement, adhesives, welding, or the like. As shown in FIGS. 4A and 4B, for example, sleeve 110 can include projections 1108 configured to engage openings 1024 of housing 102. Sleeve 110 is configured to hold a medicament chamber 114, which can include a needle 116 at a distal end of medicament chamber 114. In certain exemplary embodiments, medicament chamber 114 can include, for example, a separate glass ampule and a needle, or a pre-filled syringe, or sleeve 110 itself can include an integral medicament chamber. Preferably, a plunger 1140 is provided in the medicament chamber 114. Plunger 1140 is in association with a ram 1132 of firing mechanism 112. During an injection, ram 1132 is urged by an energy source of firing mechanism 112 to displace plunger 1140 distal, deeper into medicament chamber 114, dispensing the medicament through needle 116. Needle 116 can include an injecting tip 1160 that can be configured to penetrate the skin of a user and a hollow bore that is in fluid communication with medicament chamber 114 to facilitate delivery of medicament from medicament chamber 114 to a user during an injection. FIGS. 1A and 1B show injection device 100 in a pre-firing state, with cap 104 secured to outer housing 102 and injection device 100 in a pre-firing position. The operation of injection device 100, including its various stages and positions, are described in further detail below.

As shown in FIGS. 4A and 4B, sleeve 110 can include a ring-like structure 1100, a coupling arrangement 1102, and a body portion 1104. Coupling arrangement 1102 can be disposed at a distal portion of sleeve 110 and can be configured to releasably engage cap 104. For example, coupling arrangement 1102 can include threads configured to provide threaded engagement between sleeve 110 and cap 104. Further, sleeve 110 can include a body portion 1104 configured to secure medicament chamber 114. Body portion 1104 can include guides, such as grooves 1104a, configured to engage with features of guard 108 to align and guide axial displacement of guard 108. A proximal end of sleeve 110 can include a medicament chamber support 1106 configured to support and secure a proximal portion of medicament chamber 114. For example, support 1106 can be configured as a syringe support configured to hold a proximal end of syringe (e.g., finger flanges of a prefilled syringe) and can support medicament chamber 114 during the forces exerted on it during firing. Further, support 1106 can include an elastomer or a rubber, and can be configured to at least partially absorb the shock or a force exerted on medicament chamber 114 during an injection. Additionally, sleeve 110 can include various features, such as projections 1108, configured to couple sleeve 110 to outer housing 102. For example, projections 1108 can to concentrically symmetrical and configured to engage openings 1024 in outer housing 102 to secure sleeve 110 to outer housing 102. In an exemplary embodiment, projections 1108 can be disposed on legs 1110, which can be concentrically symmetrical and configured to engage with features of guard 108. Additionally, sleeve 110 can include locking features, such as locking projections 1112, disposed on legs 1114, which can be concentrically symmetrical, and can be configured to engage firing mechanism 112 in locking out injection device 100 to prevent a user from attempting to use an already-fired injection device 100.

Ring-like structure 1100 can include several features configured to engage sleeve 110 with glass medicament chamber 114, firing mechanism 112, and guard 108. For example, ring-like structure 1100 can include an opening 1116 through which needle 116 can be received. Further, ring-like structure 1100 can include concentrically symmetrical openings 1118 which can be configured to receive legs of guard 108. Additionally, ring-like structure 1100 can be configured to support a distal portion of medicament chamber 114 and engage firing mechanism 112 in preventing further axial displacement of firing mechanism 112 during dispensing of the medicament. Operation of these components are described in further detail below.

Figure 9A:
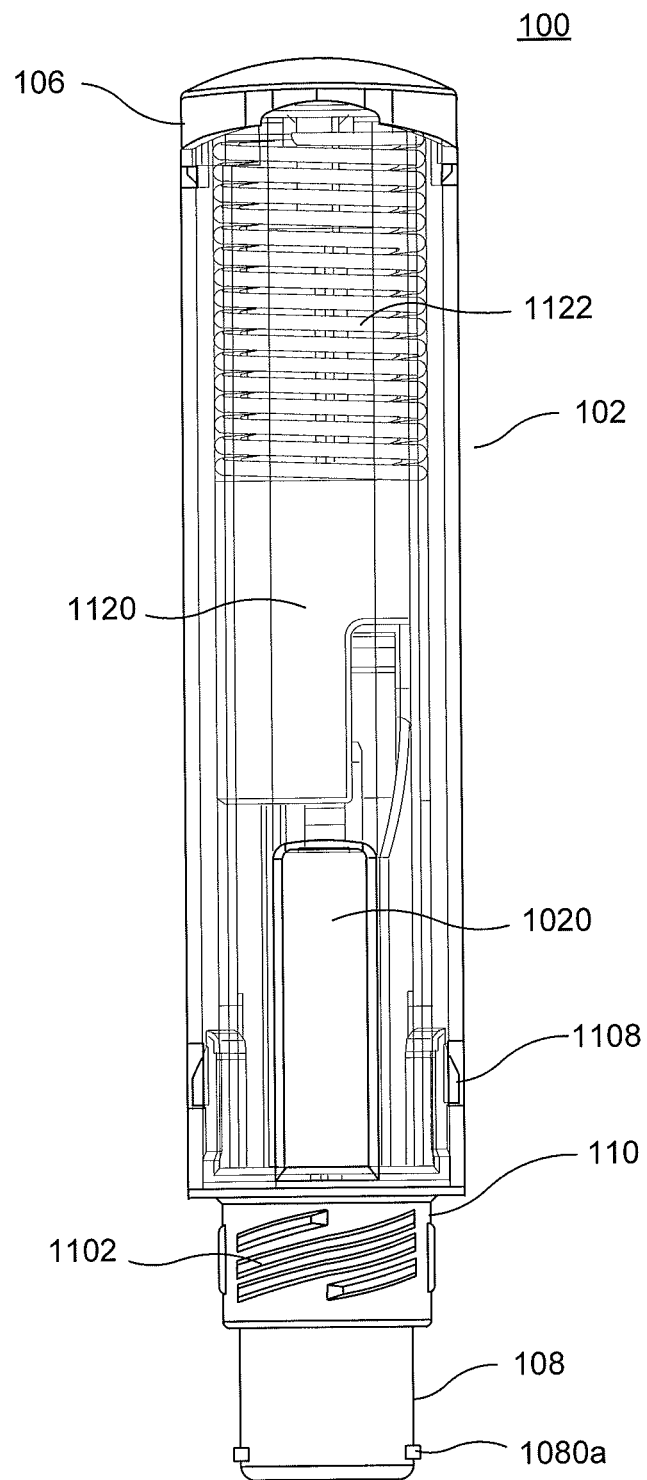
Figure 10A:
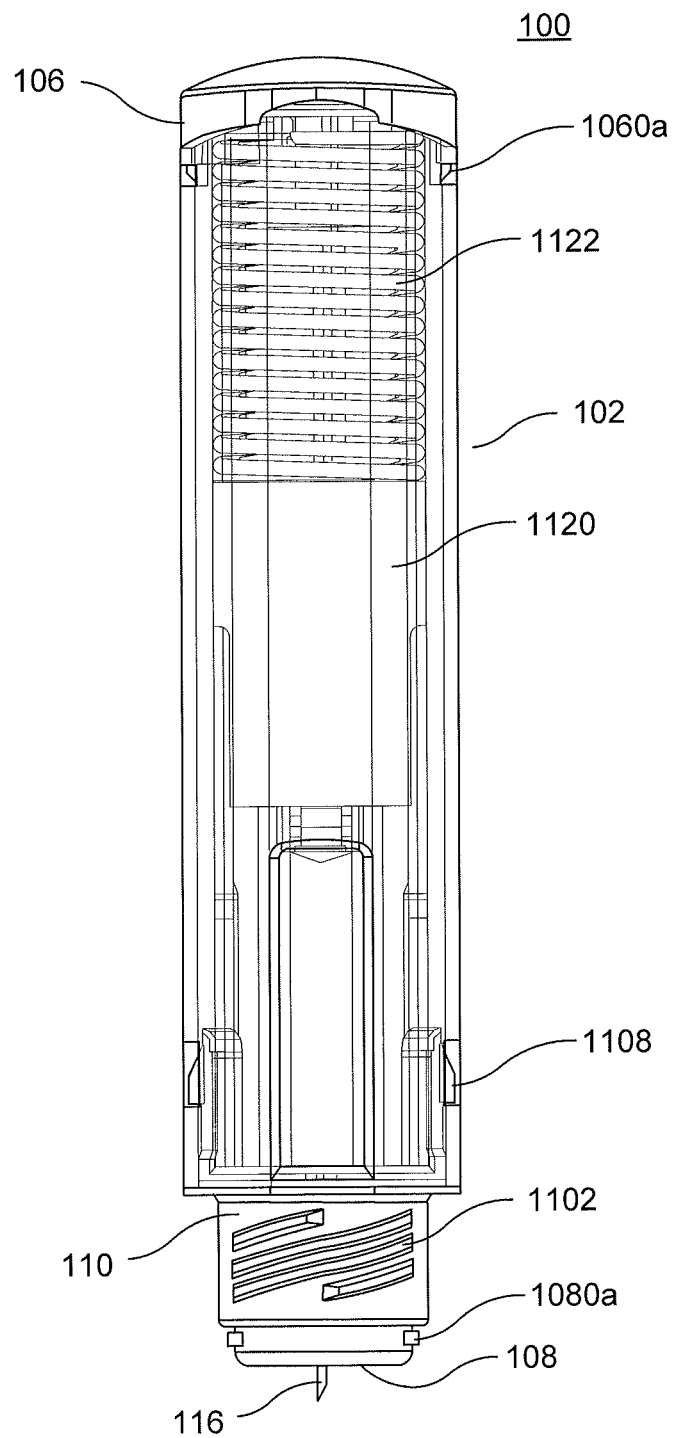

As shown in FIGS. 5A and 5B, injection device 100 preferably includes a guard 108 slidably mounted at least partially within outer housing 102 and configured to engage firing mechanism 112 to actuate firing of injection device 100. Preferably, guard 108 is slidably movable relative to outer housing 102 between an extended (e.g., a distal, protective) position and a retracted (e.g., proximal) position. In the extended position, guard 108 preferably covers needle 116, and in the retracted position, needle 116 is not covered by guard 108 and is thereby exposed. For example, FIG. 9A shows guard 108 in the extended position, and FIG. 10A shows guard 108 in the retracted position. Preferably, guard 108 is resiliently biased toward the extended position via a spring 118, which can be disposed, for example, between a distal surface of ring-like structure 1100 of sleeve 110 and an interior surface of a distal end of guard 108.

In an exemplary embodiment, guard 108 includes a distal portion 1080 and legs 1082. In an exemplary embodiment, the distal end of guard 108 preferably includes a skin-contacting member. Distal portion 1080 includes an opening through which needle 116 can pass and projections 1080a. Projections 1080a can be configured to about a distal edge of sleeve 110 so as to limit the proximal displacement of guard 108. For example, as guard 108 is proximally displaced under a force applied by a user during an injection, projections 1080a will come into contact with the proximal edge of sleeve 110 so that guard 108 cannot be further proximally displaced. Further, projection 1080a can be configured to engage engagement feature 1042 of cap 104 so that guard 108 cannot be proximally displaced when engaged with engagement feature 1042 of cap 104.

Legs 1082 of guard 108 are preferably configured to be received in openings 1118 of ring-like structure 1100. Further, legs 1082 can include ridges 1082a configured to engage grooves 1104a of sleeve 110, to facilitate alignment and guiding of legs 1082 as guard 108 is axially displaced. As shown in the exemplary embodiments of FIGS. 5A and 5B, legs 1082 also preferably include firing-initiation members, such as camming surfaces 1084 at a proximal end of legs 1082. In an exemplary embodiment, legs 1082 and camming surface 1084 can be concentrically symmetrical. Camming surfaces 1084 are configured to engage firing mechanism 112 in initiating a firing of injection device 100 and performing an injection of the medicament stored in medicament chamber 114. The proximal ends of legs 1082 can also be sloped to facilitate legs 1082 being received within firing mechanism 112 when guard 108 is displaced from the extended position to the retracted position. Preferably, legs 1082 include projections 1086 disposed on springs 1088 which can also include sloped surfaces 1088a. Projections 1086 can be configured to engage proximal surfaces of legs 1110 of sleeve 110 to oppose a force exerted by spring 118, which biases guard 108 in the extended position. Further, sloped surfaces 1088a can be configured to engage an interior surface of legs 1110 of sleeve 110 so that as guard 108 is displaced from the extended position to the retracted position, sloped surfaces 1088a engage the interior surfaces of legs 1110 so as to bias springs 1088 towards an interior of injection device 100.

As shown in FIG. 1B, injection device 100 also preferably includes firing mechanism 112. Firing mechanism 112 can include a ram assembly 1120 slidably mounted within housing 102 and an energy source 1122. In an exemplary embodiment, the energy source 1122 preferably includes a compression spring 1122, however, other suitable energy source can be used, such as an elastomer or compressed-gas spring, or a gas generator, or other suitable energy storage members. In FIG. 1A, ram assembly 1120 is in a pre-firing proximal-most position. During an injection, ram assembly 1120 is urged distally by energy released by energy source 1122. Once an injection is completed, firing ram assembly 1120 is disposed in a distal position (as shown in FIG. 12B). In this distal position, guard 108 is locked-out so that a user cannot attempt a subsequent injection. Although shown as a single piece, ram assembly 1120 can be a multiple piece assembly that can be coupled together, for example, via a snap-fit connection, a press-fit connection, a threaded engagement, adhesives, welding, or other suitable couplings. Ram assembly 1120 preferable includes various features that can be configured to facilitate firing of injection device 100 to dispense the medicament stored in medicament chamber 114. According to certain exemplary embodiments of the present disclosure, a trigger mechanism of injection device 100 can include ram assembly 1120, the trigger member and trigger retaining portion 1022, and ram retaining holding member 1060.

Figure 6A:
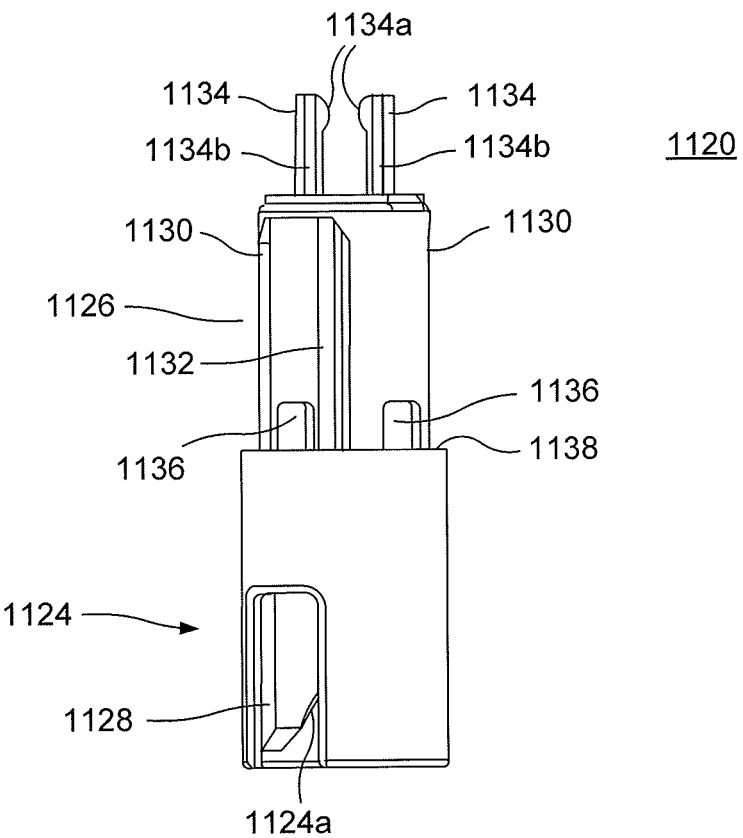
FIGS. 6A and 6B are side and perspective views respectively of a ram assembly of an exemplary injection device according to an exemplary embodiment of the present disclosure.
Figure 6B:
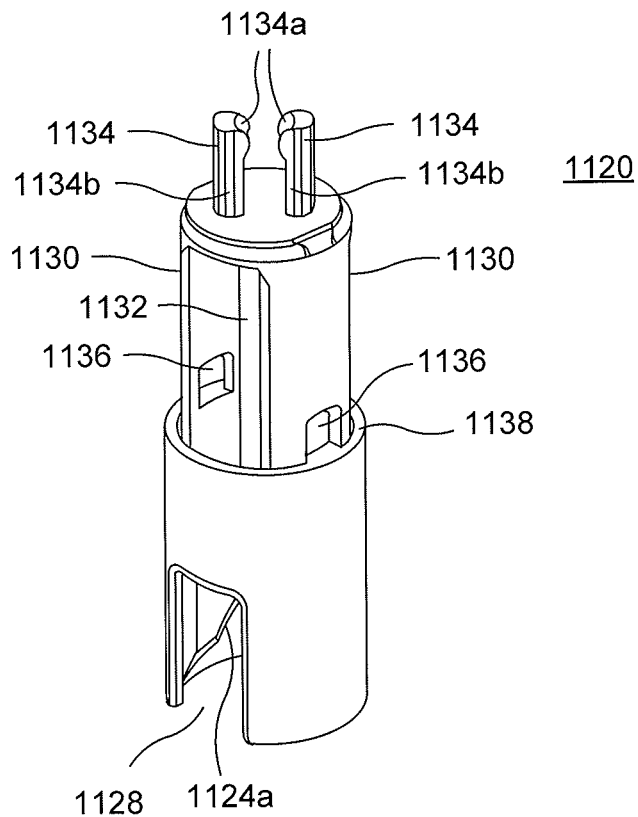
Figure 7:
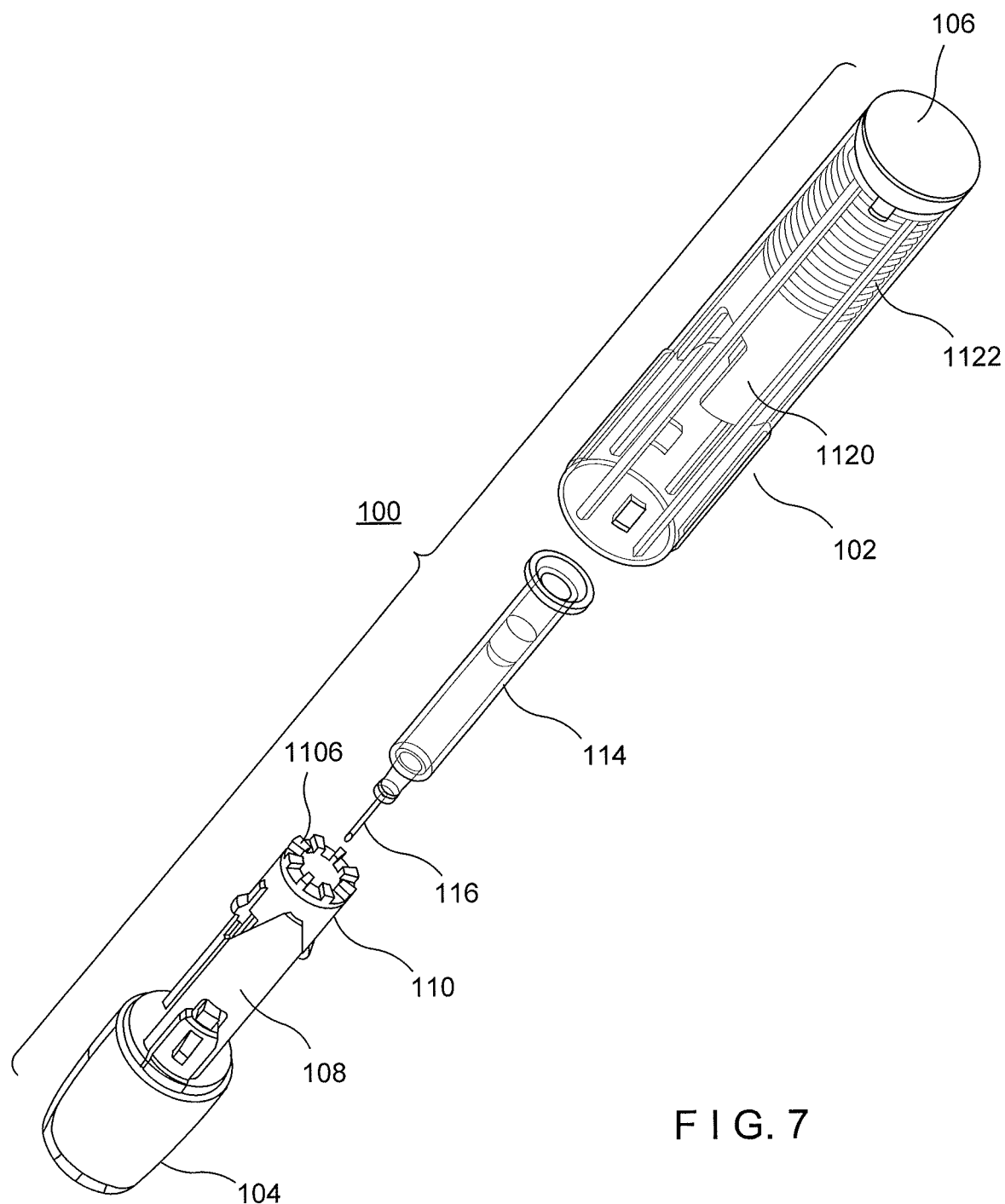
FIG. 7 is an exploded view of an exemplary injection device according to an exemplary embodiment of the present disclosure.
Figure 16:
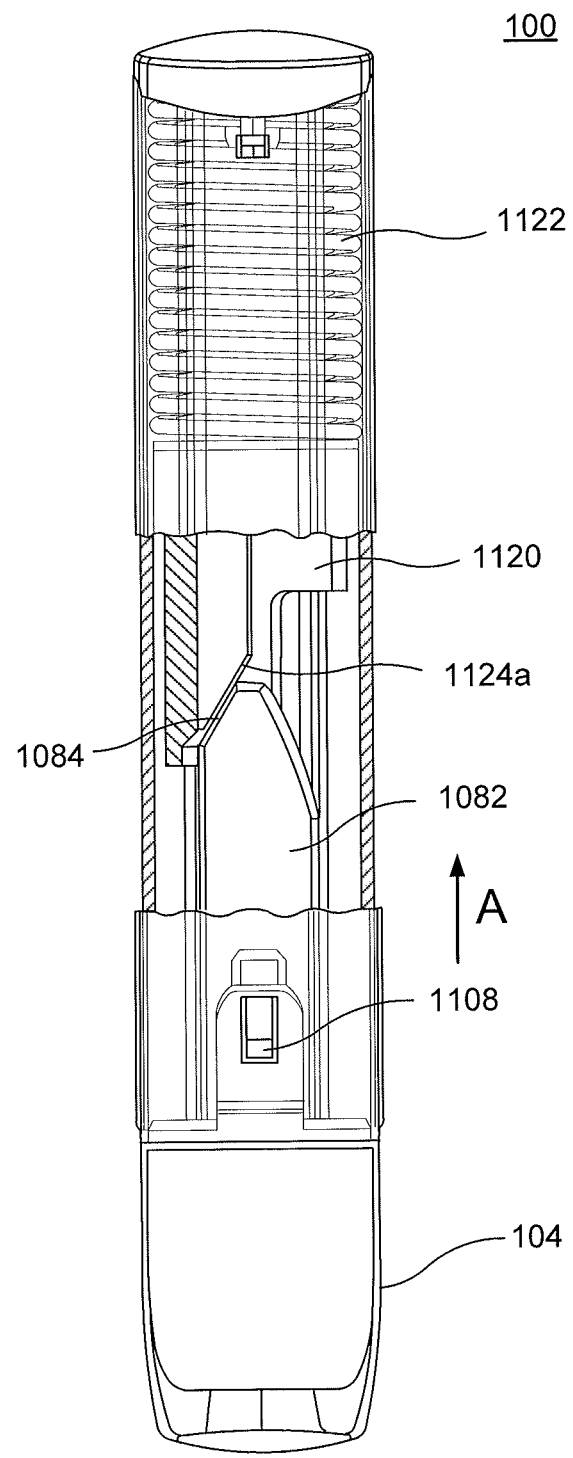
FIG. 16 shows a side view of an exemplary injection device according to an exemplary embodiment of the present disclosure.

As shown in FIGS. 6A and 6B, in an exemplary embodiment, ram assembly 1120 can include a distal portion 1124 and a proximal portion 1126 separated by a feature 1138, such as a lip, a ledge, that can be configured to act as a seat for energy source 1122. In an exemplary embodiment, compression spring 1122 can be disposed between a proximal end of housing 102 and feature 1138. Distal portion 1124 can be substantially cylindrical and can be configured to concentrically receive at least a portion of sleeve 110 and guard 108. Distal portion 1124 can also include openings 1128 configured to receive legs 1110 of sleeve 110 and projection 1086 of guard 108. An interior surface of distal portion 1124 can include camming surfaces 1124a configured to engage camming surfaces 1084 of guard 108. FIG. 16 shows engagement of camming surfaces 1124a with camming surfaces 1084 of guard 108 in a pre-fired state. As guard 108 is moved proximally during an injection, the axial movement of guard 108 is translated into a rotational movement of ram assembly 1120 via the engagement of camming surfaces 1124a and 1084.

Proximal portion 1126 preferably includes legs 1130, a ram 1132, and a trigger engagement member, such as, e.g., projections 1134. Although the trigger engagement member is shown as projections 1134, alternative implementations are contemplated. The trigger engagement member can include any feature (e.g., an elongated tab, a recess, a protrusion, a bulge, a thread, etc.) that can be held by ram retaining member in the pre-firing state, and released upon rotation of the trigger engagement member. For example, the ram retaining member can be shaped such that it prevents axial movement of the trigger engagement member in a first position, but releases trigger engagement member in a rotationally translated second position. Camming surfaces 1124a and 1084 are preferably oriented at an angle with respect to the longitudinal axis of the device to achieve a selected force and throw required to depress the guard 108 from the extended to the retracted position to fire the device. In some embodiments, the camming surfaces are angled at between 15° and 75° with respect to the axis, and more preferably between about 20° and 45°. In one embodiment, the camming surfaces are angles at about 30° with respect to the axis.

Figure 15:
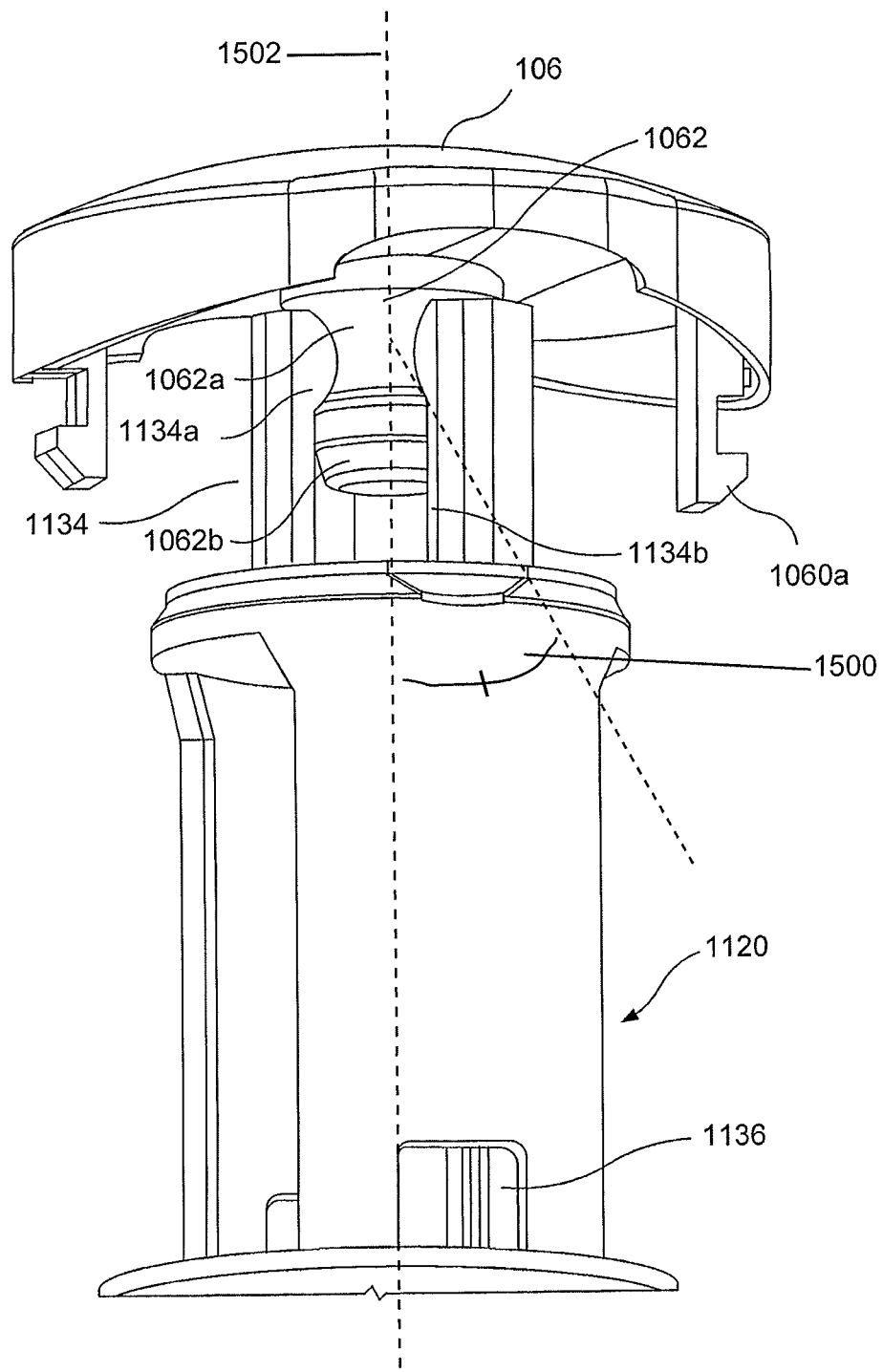
FIG. 15 shows a close-up view of an engagement of a trigger engagement member and a ram retaining member of an exemplary injection device according to an exemplary embodiment of the present disclosure.

As shown in FIGS. 6A and 6B, legs 1130 include openings 1136 configured to engage locking projections 1112 of sleeve 110. For example, locking projections 1112 of sleeve 110 can engage openings 1136 of firing mechanism 112 after injection device 100 has been fired, locking-out injection device 100 so that a user cannot initiate another firing of injection device 100. Ram 1132 is configured to be in association with plunger 1140, and distally displace plunger 1140 under the force of energy source 1122 to dispense the medicament contained in medicament chamber 114 during an injection. Additionally, projections 1134 can be disposed at a proximal end of proximal portion 1126 and can be configured to engage opening 1022 of housing 102 and ram holding member 1062 of housing end/end cap 106. The engagement of projections 1134 with opening 1022 and ram holding member 1062, as well as the alignment of projections 1134 within opening 1022 can control and enable firing of injection device 100. For example, projections 1134 can include bulges 1134a configured to engage groove 1062a of ram holding member 1062, and shapes 1134b configured to engage bulge 1062b of ram holding member 1062. As noted above, projections 1134 and ram holding member 1062 preferably include circular cross-sections to allow rotation of ram assembly 1120 during firing of injection device 100. FIG. 15 shows a closeup view of the engagement of trigger engagement member (e.g., projections 1134) with ram holding member 1062.

In certain embodiments, the engagement of the ram holding member 1062 of housing end/end cap 106 with projections 1134 of ram assembly 1120 creates a latch retention angle 1500. In one embodiment, latch retention angle 1500 is defined by axis 1502 and the contact surface of a distal portion of groove 1062a of ram holding member 1062 of housing end/end cap 106 and bulge 1134a of projections 1134 of ram assembly 1120. In certain embodiments, projections 1134 and ram holding member 1062 are sized and shaped to create, when engaged, a latch retention angle 1502 of about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, about 50°, about 510, about 52°, about 53°, about 54°, about 55°, about 56°, about 57°, about 58°, about 59°, about 60°, about 61°, about 62°, about 63°, about 64°, about 65°, about 66°, about 67°, about 68°, about 69°, about 70°, about 71°, about 72°, about 73°, about 74°, about 75°, about 76°, about 77°, about 78°, about 79°, about 80°, about 81°, about 82°, about 83°, about 84°, about 85°, about 86°, about 870, about 88°, about 89° or any range determinable from the preceding angles (for example, about 39° to about 41° or about 79° to about 81°).

Figure 8A:
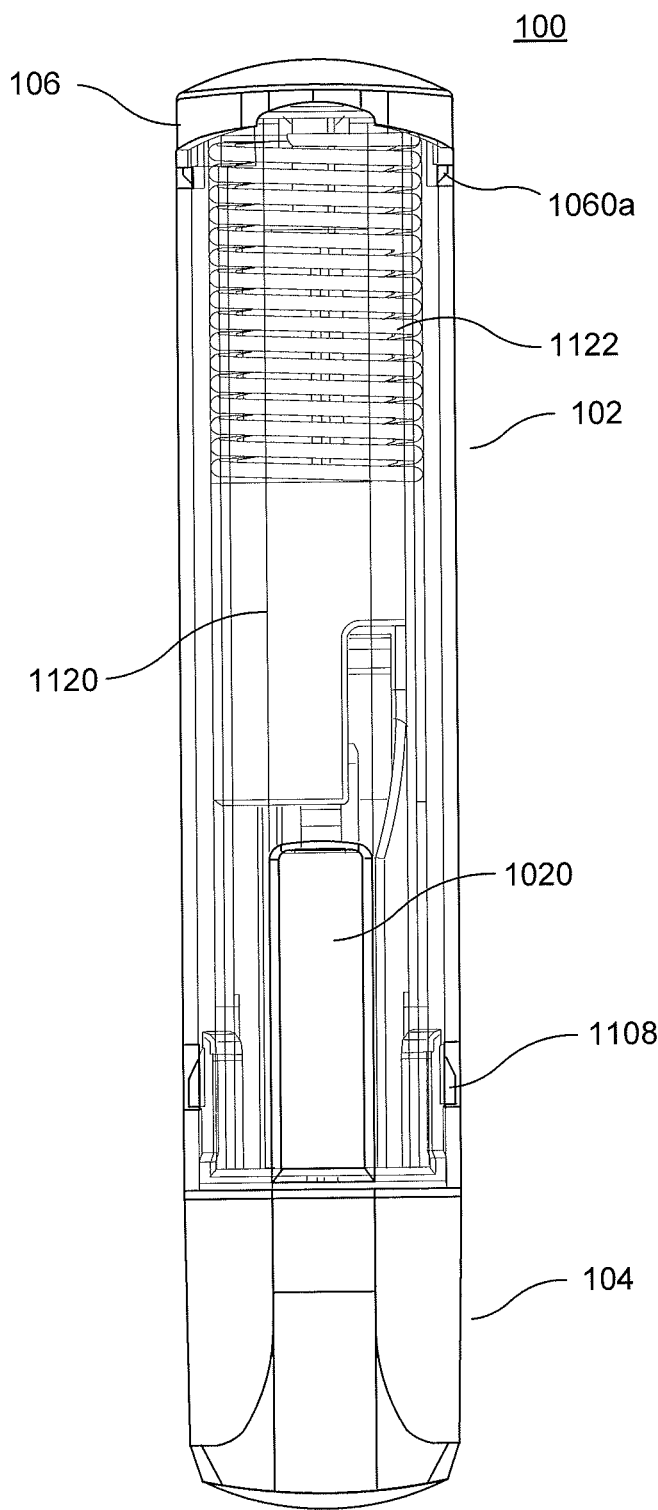
FIGS. 8A-13C are side, cross-sectional, and internal views of an operation of an exemplary injection device according to an exemplary embodiment of the present disclosure.
Figure 8B:
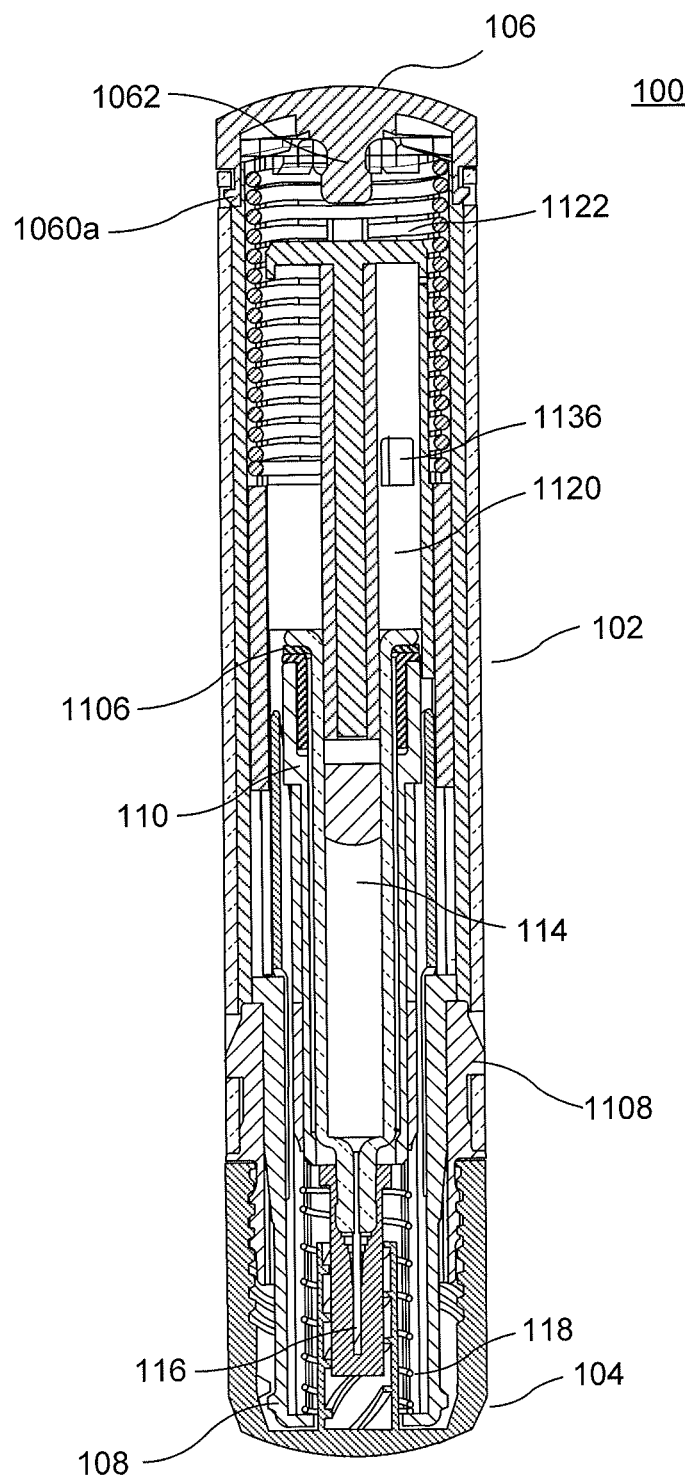

FIGS. 8A-12B show the various stages and states of exemplary injection device 100. FIGS. 8A and 8B show injection device 100 in a pre-firing "safeties-on" configuration. For example, in the pre-firing "safeties-on" configuration, injection device 100 is in a pre-firing state and cap 104 is affixed to injection device 100. In this configuration, guard 108 is in the extended position under force of spring 118 covering needle 116, ram assembly 1120 is in its proximal position, and energy source 1122 has not released its energy. Further, in this state, projections 1134 of ram assembly 1120 are engaged with opening 1022 and aligned in the first position 1022a (e.g., pre-firing condition) of opening 1022. Further, projection 1134 are also engaged with ram holding member 1062 of housing end/end cap 106. In this position, the engagement of projections 1134 with ram holding member 1062 of housing end/end cap 106 oppose the force of energy source 1122. Further, with projections 1134 aligned within the first position 1022a of opening 1022, the lateral sides of opening 1022 (formed by the proximal end of housing 102) prevent projections 1134 from splaying open and disengaging ram holding member 1062 under the force of energy source 1122.

Figure 9B:
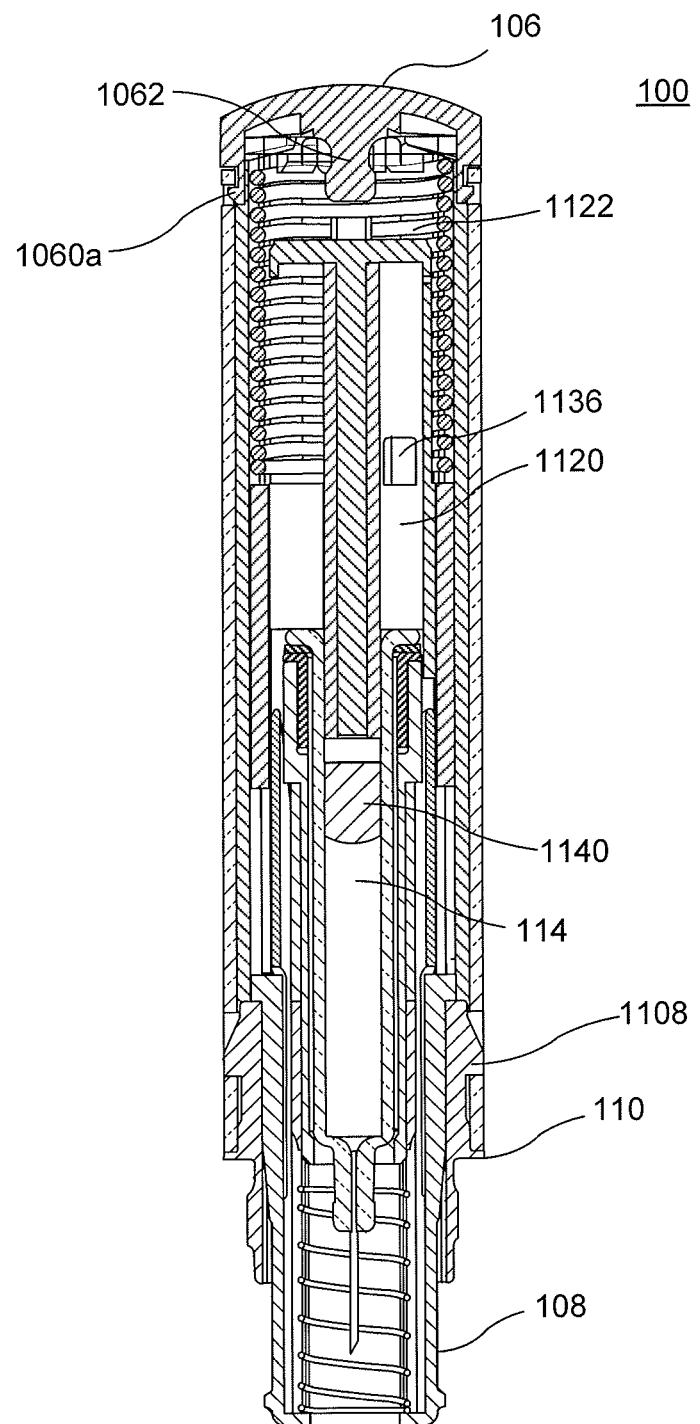
Figure 13A:
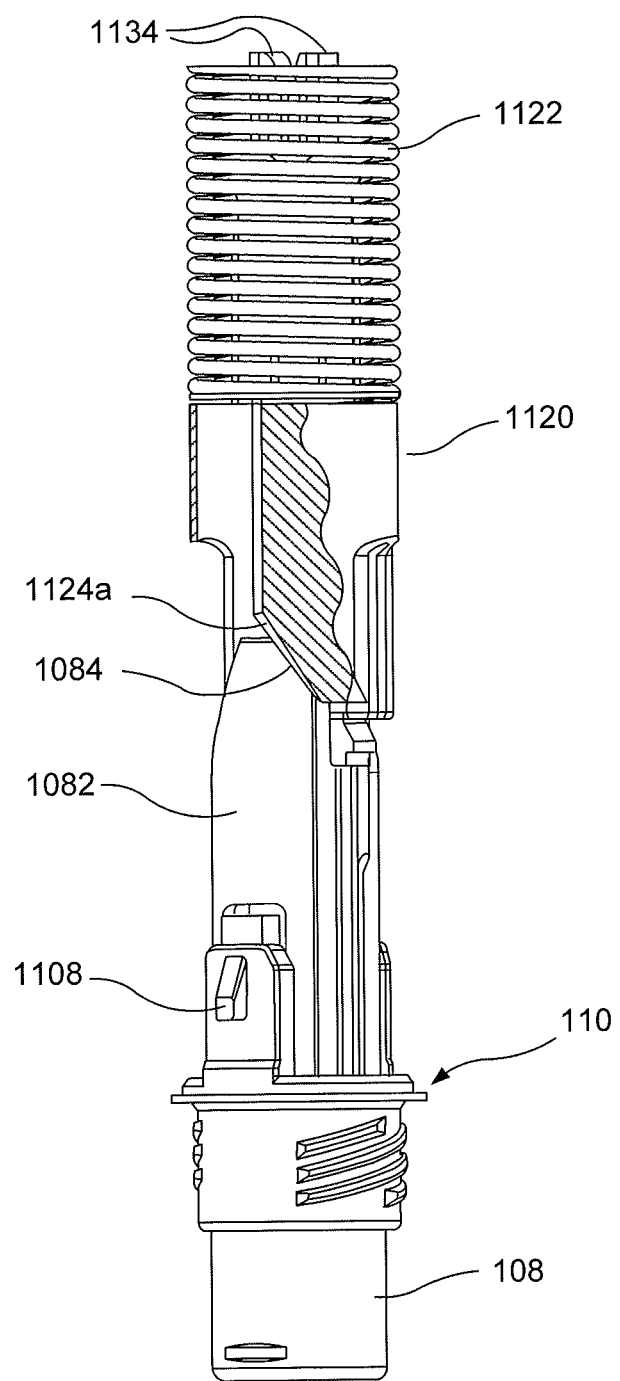

In FIGS. 9A and 9B, injection device 100 is shown in a pre-firing "ready-to-use" state. FIG. 13A shows many of the internal components of injection device 100 in this pre-firing "ready-to-use" state without showing housing 102. For example, safety member 104 has been removed, but the user has not otherwise initiated an injection. Accordingly, in this state, the medicament is still in medicament chamber 114, guard 108 remains in an extended position covering needle 116, energy source 1122 has not released the energy that its has stored, and projections 1134 of ram assembly 1120 remains engaged with ram holding member 1062 and aligned in the first position (1022a) of opening 1022.

Figure 10B:
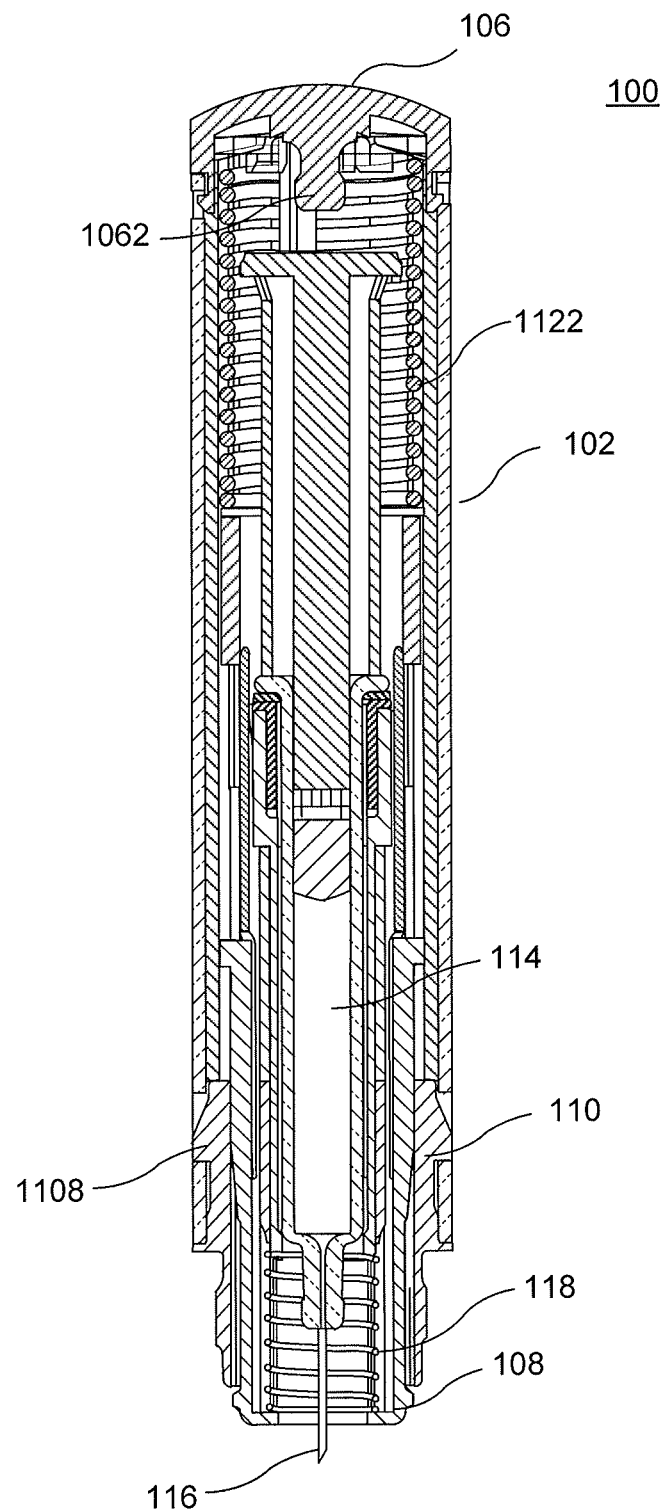
Figure 13B:
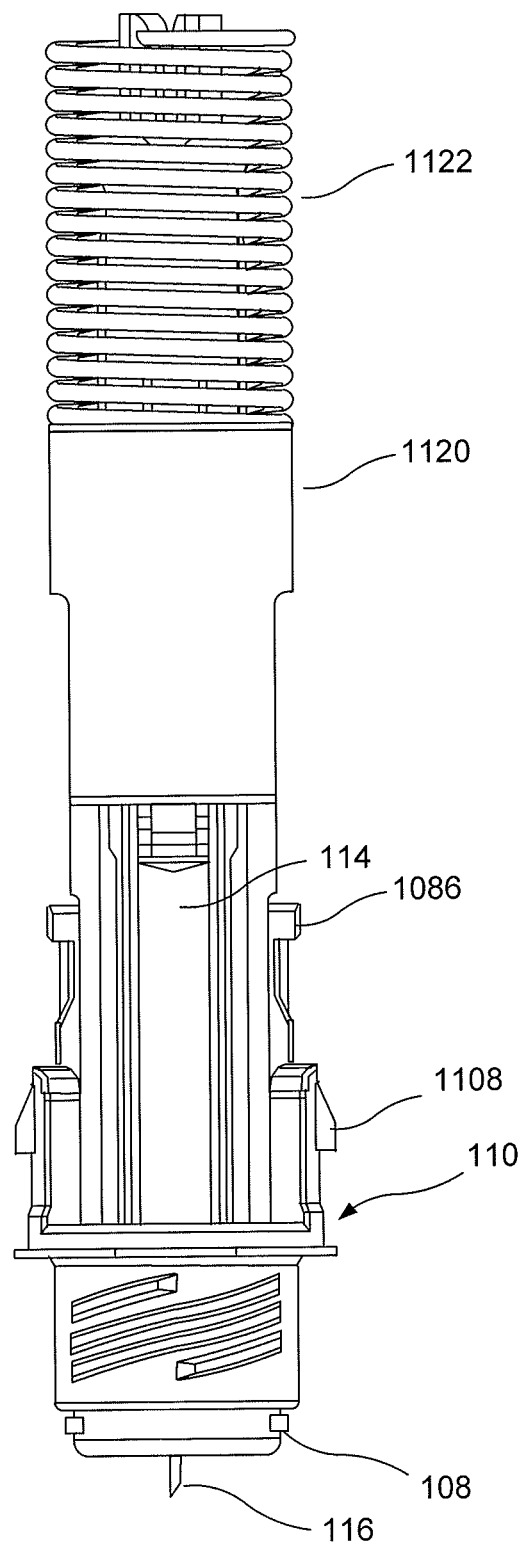

FIGS. 10A and 10B show injection device 100 in a triggered or "just-used" state. FIG. 13B shows many of the internal components of injection device 100 in this triggered or "just-used" state without showing housing 102. In this state, guard 108 has been proximally slidably displaced (e.g., by application of a force on the distal end of guard 108) from the extended position to the retracted position, thereby exposing needle 116. Energy source 1122 is just beginning to release its stored energy (e.g., the exemplary compression spring remains compressed), and ram assembly 1120 remains in the proximal-most position. Injection device 100 may be in this state, for example, during an initial stage of use by a user. For example, this can be observed when the user has pressed guard 108 of injection device 100 against an injection site to perform an injection. Accordingly, the force exerted by the user in pressing guard 108 of injection device 100 against the injection site may have proximally displaced guard 108 against the force of spring 118, thereby displacing guard 108 into the retracted position and exposing needle 116 to penetrate the user's skin at the injection site.

In this triggered state shown in FIG. 10B, guard 108 has been displaced into the retracted position, camming surfaces 1084 of guard 108 engage camming surfaces 1024a disposed on the interior of ram assembly 1120, thereby camming ram assembly 1120 (see FIG. 16). This camming action rotates ram assembly 1120, causing projections 1134 to become unaligned with the first position of opening 1022 and become aligned with the second position of opening 1022. In this position, projections 1134 are no longer restrained from splaying open by the lateral walls of opening 1022. Accordingly, projections 1134 splay open under the force of, energy source 1122, causing projections 1134 to disengage with ram holding member 1062 of housing end/end cap 106. The disengagement of projections 1134 with ram holding member 1062 allows ram assembly 1120 to be distally slidably displaced relative to housing 102 under the force generated by energy source 1122. The distal displacement of ram assembly 1120 is preferably restrained by ram assembly 1120 abutting a proximal surface of ring-like structure 1100 of sleeve 110.

Figure 11A:
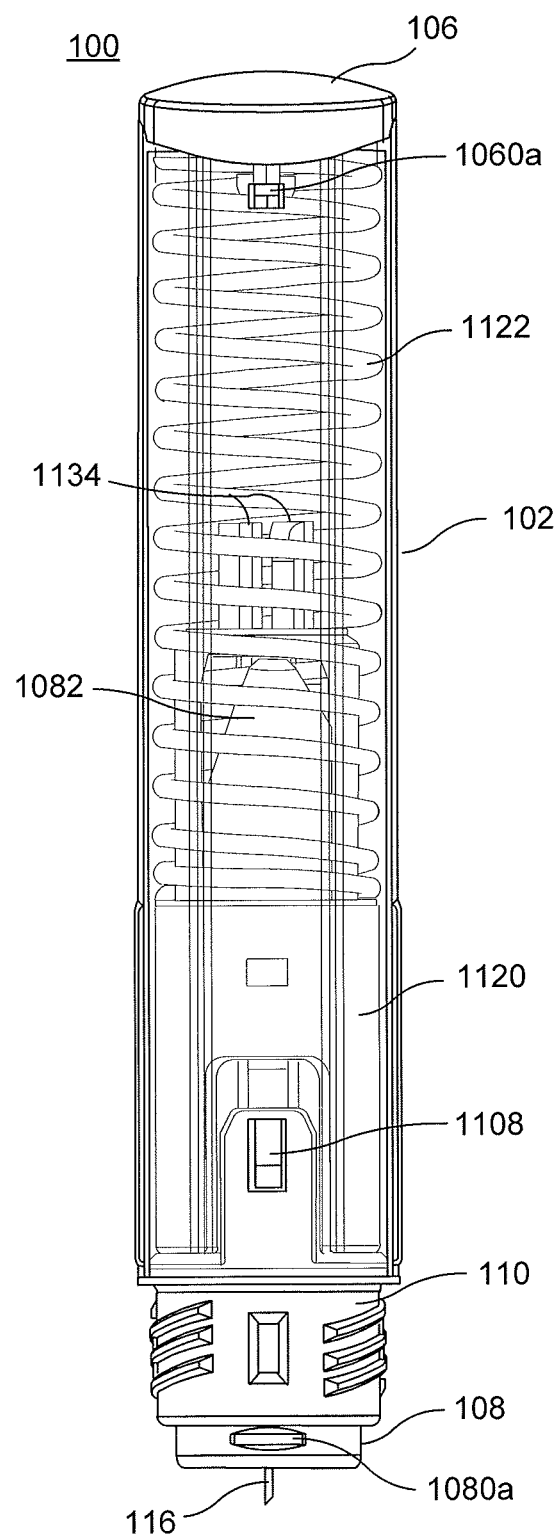
Figure 11B:
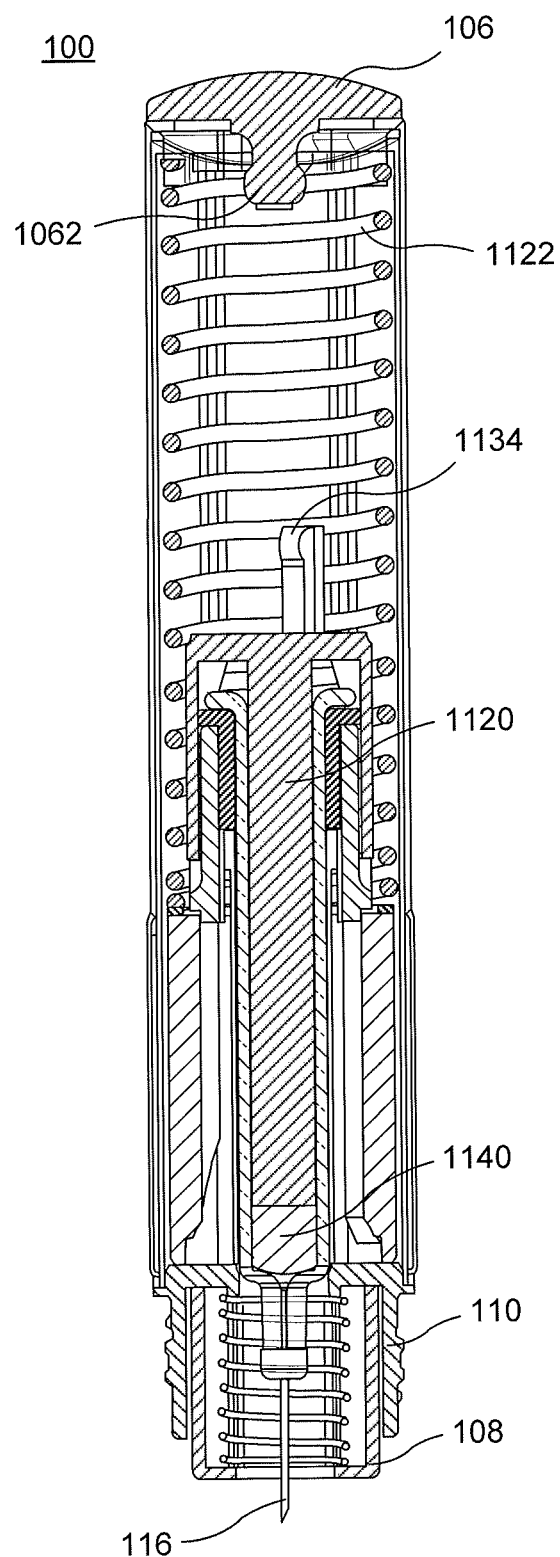

FIGS. 11A and 11B show injection device 100 in a "just-injected" state. This state follows the disengagement of projections 1134 with ram holding member 1062 and the distal displacement of ram assembly 1120 described above. In this state, energy source 1122 (e.g., a compression spring) has released its energy, thereby distally displacing ram assembly 1120. Further, guard 108 remains compressed in the retracted position. This state may be observed during use of injection device 100 immediately following the state shown in FIGS. 10A and 10B. As described above, camming of ram assembly 1120 aligns projections 1134 with the second position defined by opening 1022, allowing projections 1134 to splay open and disengage ram holding member 1062 under the force released by energy source 1122. Accordingly, energy source 1122 has released at least some, if not all, of its stored energy (e.g., compression spring is less compressed), and ram assembly 1120, as well as ram 1132, has been distally displaced into a distal position. The distal displacement of ram 1132 urges plunger 1140 in a distal direction, injecting the medicament into the user by dispensing the medicament in medicament chamber 114 through needle 116 and into the user. Although the injection has preferably been completed in this state, injection device 100 is still likely pressed against the injection site since guard 108 remains in a retracted position exposing needle 116. Further, this distal displacement of ram assembly 1120 preferably positions ram assembly 1120 such that it is displayed in window 1020 of housing 102. In an exemplary embodiment, after the distal displacement of ram assembly 1120, it is disposed between medicament container 114 and housing 102 such that it is entirely occluding window 1020 so that only ram assembly 1120 is visible through window 1020, and medicament container 114 is no longer visible (e.g., ram assembly is disposed between medicament container 114 and window 1020). Further, ram assembly 1120 can have a color (as described above) that would be a clear indicator to a user that injection device 1.00 has been used, and different than the other colors visible from the outside of the injector before firing.

Figure 12A:
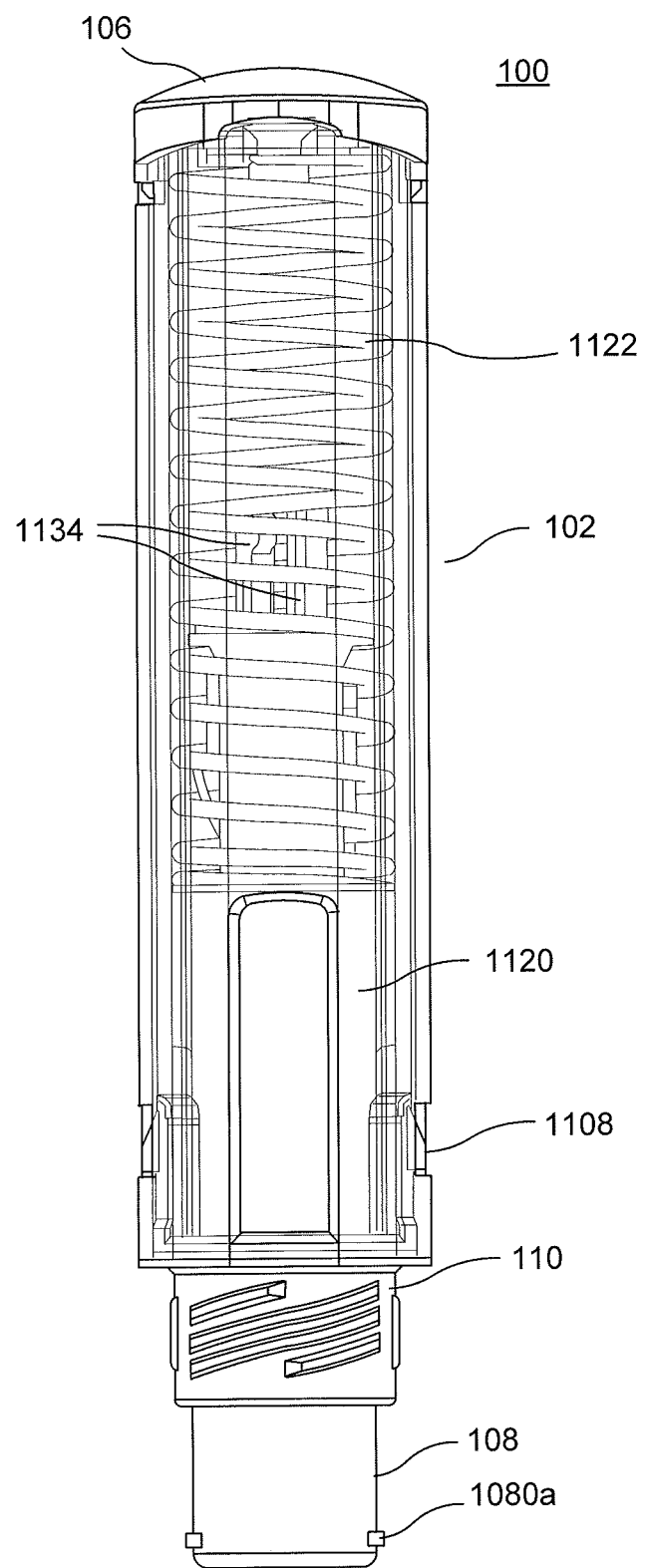
Figure 12B:
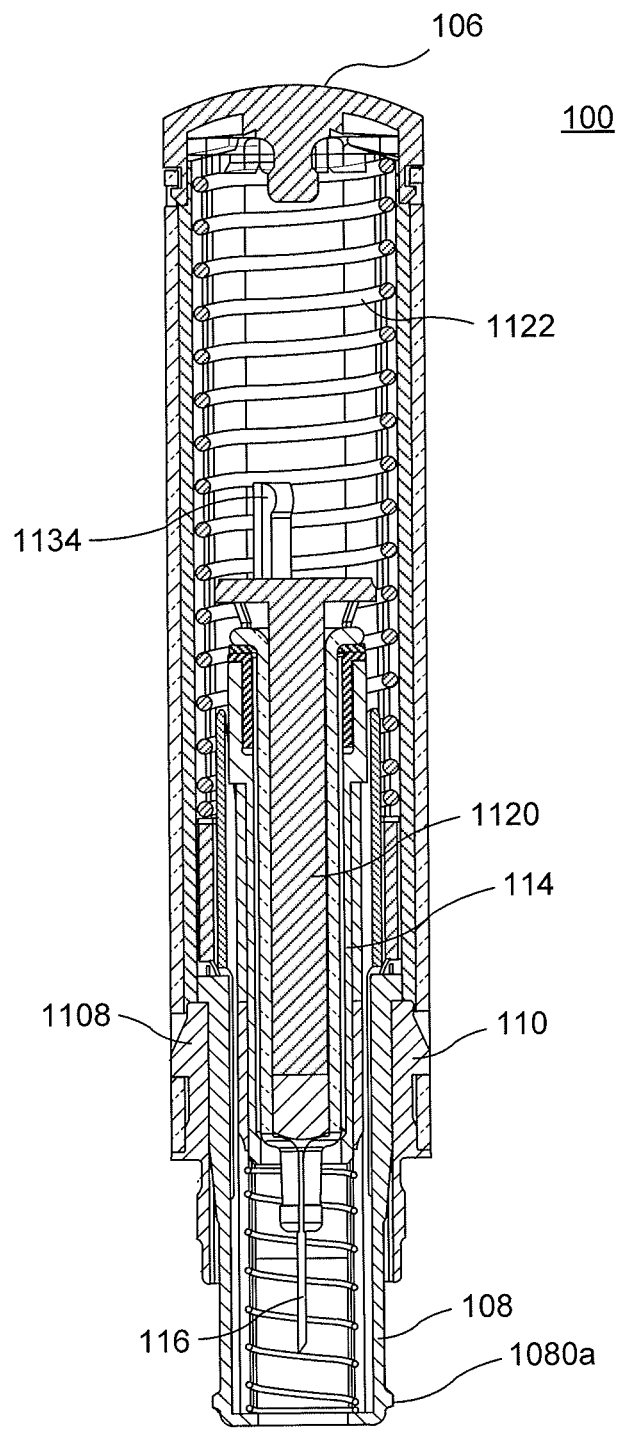
Figure 13C:
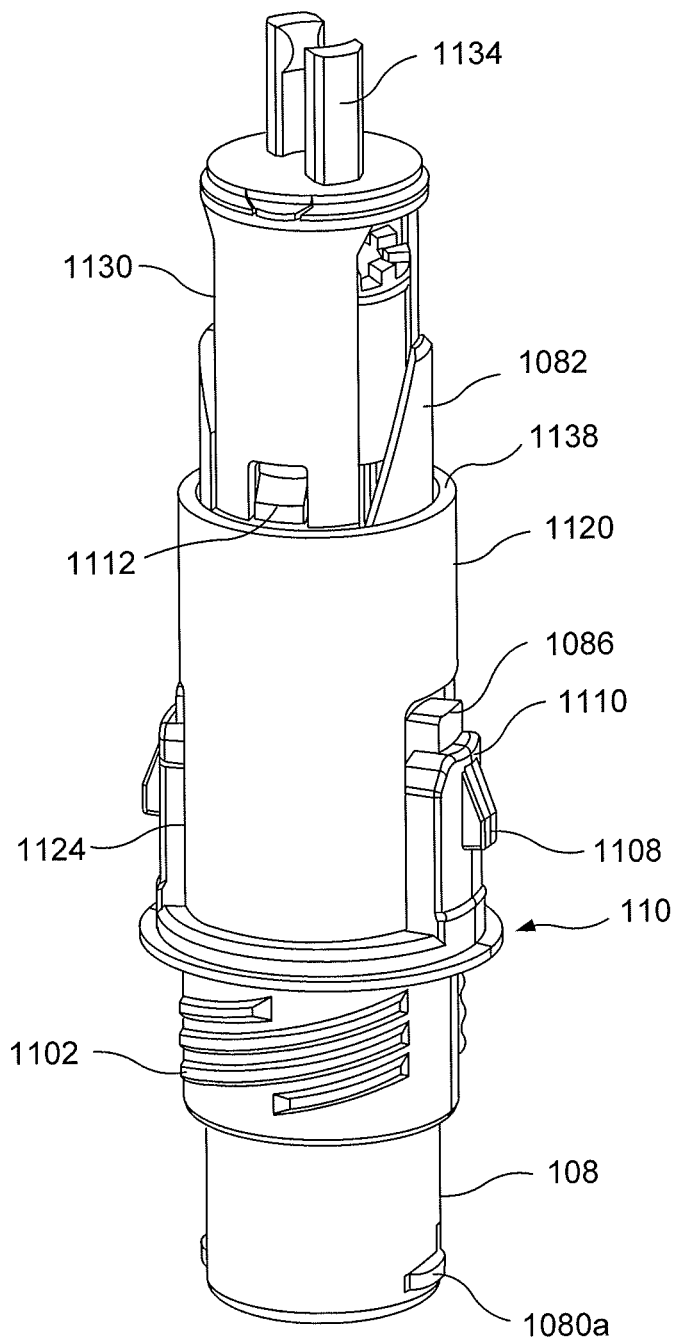

FIGS. 12A and 12B show injection device 100 in a "locked-out" state. FIG. 13C shows many of the internal components of injection device 100 in this "locked-out" state without housing 102. The state can be observed, for example, after the user has removed injection device 100 from the injection site. In this state, nothing is restraining guard 108 in the retracted position against the force of spring, and accordingly, guard 108 is distally displaced from the retracted position to the extended position under the force of spring 118, thereby covering needle 116. As guard 108 moves distally from the retracted position to the extended position under the force of spring 118, projections 1086, which are disposed on springs 1088 biased in an outward direction, engage an openings created between proximal surfaces of legs 1110 of sleeve 110 and proximal walls of openings 1128. Accordingly, the association of projections 1086 with the proximal walls of openings 1128 prevents guard 108 from being displaced proximally, and the association of projections 1086 with the proximal surfaces of legs 1110 prevents guard 108 from being displaced distally. Thus, guard 108 is in a locked position, thereby "locking-out" injection device 100 such that needle 116 is covered and guard 108 is locked in place so that a user cannot attempt a subsequent injection. Afterwards, the user may affix cap 104 back onto the distal end of injection device 100.

Advantageously, this "locked-out" state is preferably not dependent on displacement of guard 108, but rather, is preferably dependent on dispensing of the medicament stored in medicament chamber 114 and/or movement of ram assembly 1120. For example, injection device 100 become locked-out in situations where the medicament is inadvertently dispensed, even if guard 108 has not been displaced. Injection device 100 can become locked-out in any instance where energy source 1122 is activated and ram assembly 1120 is distally displaced, causing ram 1132 to displace plunger 1140, thereby dispensing the medicament in medicament chamber 114. This can occur, for example, if injection device 100 is mishandled, dropped, broken, or if housing 102 is defective (e.g., the tolerances of opening 1022 are incorrect, housing 102 is cracked or otherwise compromised, etc.) such that the lateral walls of opening 1022 cannot prevent projections 1134 from splaying outward under the force of energy source 1122. Accordingly, the lock-out feature prevents a user from unknowingly performing an "injection" with an empty injection device 100, even if injection device 100 appears to be new and not used. This can be important in preventing patients from believing that they have administered an injection when in fact the injector was empty.

Figure 17:
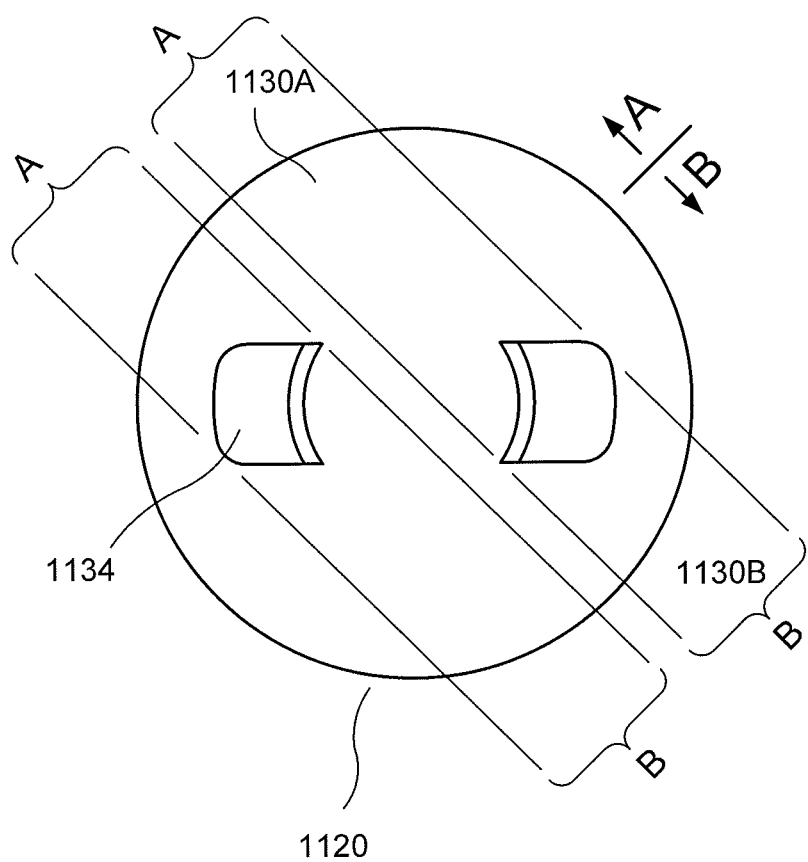
FIG. 17 shows a top view of a ram assembly of an exemplary injection device according to an exemplary embodiment of the present disclosure.

In an exemplary embodiment, many of the components of injection device 100 are preferably made of a resilient plastic or polymer, or a metal. Preferably, projections 1134 of ram assembly 1120 are oriented so that ram assembly 1120 can be molded using a single mold. For example, as shown in FIGS. 6B and 13C, projections 1134 (which are preferably concentrically symmetrical to each other) can be aligned at an angle relative to the alignment of the other features of ram assembly 1120, such as legs 1130 (which are preferably concentrically symmetrical to each other). For example, as shown in FIG. 17, a single mold can form the portion of ram assembly 1120 designated A (including all the features, components, openings, etc. 1130A), and a single mold can form the portion of ram assembly designated B (including all the features, components, openings, etc. 1130B). Thus, each surface of projections 1134 is preferably accessible along a direction of separating the two molds, and the two molds can be separated linearly without a concave portion of projections 1134 facing orthogonal to the separation direction impeding separation and removal of the molds.

Further, cap 104 can be configured helically so that it can be molded without a hole/opening. For example, cap 104 can include threads 1044 that permit cap 104 to be threadedly removed from a mold. Further, outer housing 102 can include a translucent material to allow users to view the inner workings of injection device 100, and ascertain if it is malfunctioning (e.g., as shown in FIGS. 1A, 7, 8A, 9A, 10A, 11A, 12A, and 16). Additionally, injection device 100 can include various gripping elements, such as ridges, pads, contours, or the like, to make injection device 100 more ergonomic, easy to use, and comfortable to the user. Further, injection device 100 can include markings, such as a sticker, brand markings, drug information, numerals, arrows, or the like, to indicate the steps needed to perform an injection, and areas for promotional markings such as brand and logo designations.

FIG. 18 shows another exemplary embodiment of injection device. As shown in FIG. 18, ram assembly 1120 can include trigger engagement member that takes the form of a seat or ledge 1120b. Seat 1120b can engage a retaining portion, such as ledges 102a, of housing 102 in the pre-fired condition such that the engagement of ledges 102a with the seat 1120b in the pre-fired condition opposes the force of energy source 1122. When a firing of injection device 100 is initiated, ram assembly 1120 can be rotated, for example, via a camming association of guard 108 and ram assembly (such as described with respect to exemplary embodiments above) until recesses 1120a between the seats 1120b align with projections 102a in the firing condition. In the firing condition, the force of energy source 1122 is no longer opposed, allowing ram assembly 1120 to be distally displaced and dispensing the medicament in performing an injection.

All of the references specifically identified in the detailed description section of the present application are expressly incorporated herein in their entirety by reference thereto. The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments may be devised by those skilled in the art. For example, the features for the various embodiments can be used in other embodiments. In an alternative embodiment, the hosing can be fixed to the bracket, and the inner portion, defining at least the bottom of the chutes can slide in and out of the housing. Other embodiments can include different mechanisms to cause the rotation of the ram assembly to release it from the retainer portion, such as by direct rotation of the ram by a user, such as via a slide or other element accessible on the outside of the housing, or by a button that is pushed with a finger, or another transmission mechanism to rotate the ram or ram assembly. Therefore, it will be understood that the appended claims are intended to cover all such modifications and embodiments that come within the spirit and scope of the present invention.

The invention claimed is:

1. An injector, comprising:
   an injector housing;
   a container support at least partially within the injector housing, the container support including a projection configured to fix the container support relative to the injector housing;
   a medicament container associated with the container support;
   a trigger mechanism including:
      a trigger member having a retainer portion, and
      a ram assembly having a ram configured to pressurize the medicament container for expelling a medicament therefrom, the ram assembly further having a trigger engagement member configured to engage the retainer portion of the trigger member in a pre-firing condition;
   an energy source associated with the ram for powering the ram to expel the medicament; and
   a user-operable firing-initiation member operable for causing relative movement between the trigger engagement member and the retainer portion from the pre-firing condition to a firing condition in which the trigger engagement member is released from the retainer portion to allow the energy source to fire the ram,
   wherein the ram assembly includes an opening extending radially through a sidewall of the ram assembly, the opening defined by an opening sidewall and configured to receive at least a portion of the user-operable firing-initiation member.

2. The injector of claim 1, wherein the user-operable firing-initiation member includes a skin-contacting member disposed at a distal end of the injector, the skin-contacting member configured to move proximally with respect to the injector housing when a force is applied to the skin-contacting member, and
   wherein the user-operable firing-initiation member is associated with the trigger mechanism and is configured to cause axial rotation between the trigger engagement member and the retainer portion from the pre-firing condition to the firing condition upon a proximal movement of the skin-contacting member with respect to the injector housing.

3. The injector of claim 2, wherein the skin-contacting member comprises a first cam, and the ram assembly comprises a second cam, the first cam being operatively associated with the second cam for camming the second cam such that the proximal movement of the skin-contacting member with respect to the injector housing is configured to rotate the ram assembly with respect to the retainer portion so as to position the ram assembly in the firing condition.

4. The injector of claim 1, wherein the user-operable firing-initiation member comprises a skin-contacting member which includes a needle guard that is retractable and is configured to expose a needle connected to the medicament container upon proximal movement of the skin-contacting member.

5. The injector of claim 4, wherein the needle is in fluid communication with the medicament container for injecting the medicament expelled therefrom during firing.

6. The injector of claim 4, wherein the energy source and the needle are configured for jet injecting the medicament through the needle.

7. The injector of claim 6, wherein the energy source is configured to pressurize the medicament to between 90 p.s.i. and 500 p.s.i. to jet inject the medicament.

8. The injector of claim 6, wherein the energy source and the needle are configured for injecting the medicament at an average velocity of at least 1,000 cm/sec within the needle.

9. The injector of claim 1, wherein:
the trigger engagement member and the ram are in fixed association, such that rotation of the trigger engagement member rotates the ram; and
the ram assembly is associated with the user-operable firing-initiation member such that operation of the user-operable firing-initiation member rotates the ram assembly within the injector housing to the firing condition.

10. The injector of claim 9, wherein the trigger mechanism comprises a ram holding member that retains the ram assembly against action of the energy source in the pre-firing position, the retainer portion retaining the trigger engagement member, wherein the trigger engagement member is prevented from firing by the ram holding member.

11. The injector of claim 10, wherein in the firing condition, the trigger engagement member is disengaged from the retainer portion, and the energy source overcomes an engagement between the trigger engagement member and the ram holding member.

12. The injector of claim 10, wherein the ram holding member includes a projection that includes a bulge and a groove engaged with the trigger engagement member, and wherein the retainer portion is configured to at least temporarily retain engagement of the trigger engagement member with the bulge and the groove in the pre-firing condition.

13. The injector of claim 1, wherein the ram assembly is of unitary construction.

14. The injector of claim 1, wherein the ram assembly is configured to engage the container support to lock-out the injector after an injection.

15. The injector of claim 14, wherein proximal movement of the user-operable firing-initiation member is blocked by the ram assembly when the injector is locked-out.

16. The injector of claim 1, wherein a pre-firing color gamut is visible from an exterior of the injector in the pre-firing condition, the injector further comprising:
a window in the injector housing; and
an indicator having an indicator color that is absent from the pre-firing color gamut, which color is hidden from view within the injector housing in the pre-firing condition, wherein in the firing condition, the indicator color is visible through the window from the exterior of the injector for indicating that the injector has been fired.

17. The injector of claim 16, wherein the ram assembly includes the indicator.

18. The injector of claim 17, wherein the ram assembly entirely occludes the window after the injector has been fired.

19. The injector of claim 1, wherein the medicament comprises testosterone.

20. The injector of claim 1, wherein the user-operable firing-initiation member includes a locking projection configured to engage the opening sidewall wherein the locking projection engaged with the opening sidewall prevents movement of the user-operable firing-initiation member relative to the container support.

21. The injector of claim 1, wherein the container support includes a coupling arrangement configured to releasably couple to a cap.

22. The injector of claim 1, wherein the trigger engagement member radially flexes from a first position to a second position as the trigger engagement member moves from the pre-firing condition to the firing condition.

* * * * *